US009717742B2

(12) United States Patent
Parhami et al.

(10) Patent No.: US 9,717,742 B2
(45) Date of Patent: Aug. 1, 2017

(54) OXYSTEROL ANALOGUE OXY133 INDUCES OSTEOGENESIS AND HEDGEHOG SIGNALING AND INHIBITS ADIPOGENESIS

(71) Applicant: The Regents of the University of California, Oakland, CA (US)

(72) Inventors: Farhad Parhami, Los Angeles, CA (US); Michael E. Jung, Los Angeles, CA (US); Frank Stappenbeck, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/399,121

(22) PCT Filed: Mar. 15, 2013

(86) PCT No.: PCT/US2013/032693
§ 371 (c)(1),
(2) Date: Nov. 5, 2014

(87) PCT Pub. No.: WO2013/169399
PCT Pub. Date: Nov. 14, 2013

(65) Prior Publication Data
US 2015/0118277 A1    Apr. 30, 2015

Related U.S. Application Data

(60) Provisional application No. 61/643,746, filed on May 7, 2012.

(51) Int. Cl.
*A61K 31/575* (2006.01)
*A61K 35/32* (2015.01)
(Continued)

(52) U.S. Cl.
CPC ............ *A61K 31/575* (2013.01); *A61K 35/32* (2013.01); *A61K 38/1841* (2013.01);
(Continued)

(58) Field of Classification Search
None
See application file for complete search history.

(56) References Cited

U.S. PATENT DOCUMENTS 3,309,387 A    3/1967    Furst et al.
3,887,545 A    6/1975    Iacobelli et al.
(Continued)

FOREIGN PATENT DOCUMENTS

DE    10204042822    3/2006
EP    337890 A1    10/1989
(Continued)

OTHER PUBLICATIONS

International Search Report issued in PCT Application No. PCT/US2013/032693 dated Jul. 18, 2013.
(Continued)

*Primary Examiner* — Bethany Barham
*Assistant Examiner* — Barbara Frazier
(74) *Attorney, Agent, or Firm* — Mintz Levin Cohn Ferris Glovsky and Popeo, P.C.

(57) ABSTRACT

This invention relates, e.g., to a synthetic compound, Oxy133, having the structure [Formula I] or a bioactive or pharmaceutical composition comprising Oxy133 and a pharmaceutically acceptable carrier. Methods are also disclosed for using the compound or bioactive or pharmaceutical composition to treat a variety of disorders, including e.g. bone disorders, obesity, cardiovascular disorders, and neurological disorders.

(Continued)

(I)

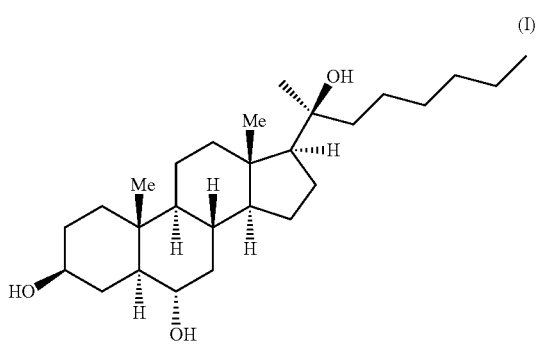

11 Claims, 15 Drawing Sheets

(51) Int. Cl.
A61K 38/18 (2006.01)
A61K 38/30 (2006.01)
A61K 45/06 (2006.01)
C07J 9/00 (2006.01)
C07J 51/00 (2006.01)

(52) U.S. Cl.
CPC .......... A61K 38/1875 (2013.01); A61K 38/30 (2013.01); A61K 45/06 (2013.01); C07J 9/00 (2013.01); C07J 51/00 (2013.01)

(56) References Cited

U.S. PATENT DOCUMENTS

| | | |
|---|---|---|
| 4,183,852 A | 1/1980 | Kaiser |
| 4,264,512 A | 4/1981 | Okamura et al. |
| 4,559,157 A | 12/1985 | Smith et al. |
| 4,608,392 A | 8/1986 | Jacquet et al. |
| 4,743,597 A | 5/1988 | Javitt et al. |
| 4,820,508 A | 4/1989 | Wortzman |
| 4,938,949 A | 7/1990 | Borch et al. |
| 4,961,922 A | 10/1990 | Shroot et al. |
| 4,992,478 A | 2/1991 | Geria |
| 5,166,320 A | 11/1992 | Wu et al. |
| 5,183,815 A | 2/1993 | Saari et al. |
| 5,219,740 A | 6/1993 | Miller et al. |
| 5,288,641 A | 2/1994 | Roizman |
| 5,723,455 A | 3/1998 | Tanabe et al. |
| 5,840,752 A | 11/1998 | Henry et al. |
| 5,929,062 A | 7/1999 | Haines |
| 6,017,904 A | 1/2000 | Reed et al. |
| 6,080,779 A | 6/2000 | Gasper et al. |
| 6,177,420 B1 | 1/2001 | Leemhuis et al. |
| 6,184,215 B1 | 2/2001 | Elias et al. |
| 6,316,503 B1 | 11/2001 | Li et al. |
| 6,420,353 B1 | 7/2002 | Lathe et al. |
| 6,436,917 B1 | 8/2002 | Droescher et al. |
| 6,518,262 B1 | 2/2003 | Leysen et al. |
| 6,586,189 B2 | 7/2003 | Forman |
| 6,863,900 B2 | 3/2005 | Kadiyala et al. |
| 6,893,830 B1 | 5/2005 | Janowski et al. |
| 6,906,069 B1 | 6/2005 | Li et al. |
| 7,060,450 B1 | 6/2006 | Tabin et al. |
| 7,196,220 B2 | 3/2007 | Pierce, Jr. et al. |
| 7,427,610 B2 | 9/2008 | Hillisch et al. |
| 8,071,575 B2 | 12/2011 | Pierce, Jr. et al. |
| 9,526,737 B2 | 12/2016 | Parhami et al. |
| 9,532,994 B2 | 1/2017 | Parhami |
| 2003/0153541 A1 | 8/2003 | Dudley et al. |
| 2004/0072806 A1 | 4/2004 | Yao et al. |
| 2004/0077613 A1 | 4/2004 | Bamberg et al. |
| 2004/0176423 A1 | 9/2004 | Paralkar |
| 2004/0235739 A1 | 11/2004 | Mahanthappa |
| 2005/0095677 A1 | 5/2005 | Liu et al. |
| 2006/0251735 A1 | 11/2006 | Parhami |
| 2006/0270645 A1 | 11/2006 | Parhami |
| 2008/0070883 A1 | 3/2008 | Nagpal |
| 2009/0202660 A1 | 8/2009 | Parhami et al. |
| 2009/0202661 A1 | 8/2009 | Kirkpatrick |
| 2009/0220562 A1 | 9/2009 | Parhami |
| 2010/0012030 A1 | 1/2010 | Todd et al. |
| 2010/0034781 A1 | 2/2010 | Parhami et al. |
| 2010/0048944 A1 | 2/2010 | Parhami |
| 2010/0105645 A1 | 4/2010 | Parhami et al. |
| 2011/0008297 A1 | 1/2011 | Parhami et al. |
| 2012/0309730 A1 | 12/2012 | Parhami et al. |
| 2015/0140059 A1 | 5/2015 | Parhami et al. |
| 2016/0159850 A1 | 6/2016 | Parhami et al. |
| 2016/0206631 A1 | 7/2016 | Parhami et al. |

FOREIGN PATENT DOCUMENTS

| | | |
|---|---|---|
| EP | 0 415 731 A2 | 3/1991 |
| GB | 869007 A | 5/1961 |
| GB | 2 320 190 A | 6/1998 |
| JP | S51-11114 B1 | 4/1976 |
| JP | 2000-508911 A | 7/2000 |
| JP | 2000-511404 A | 9/2000 |
| JP | 2002-506030 A | 2/2002 |
| JP | 2002-506817 A | 3/2002 |
| RU | 2006 103 797 A | 7/2006 |
| WO | WO-90/07936 A1 | 7/1990 |
| WO | WO-91/02805 A2 | 3/1991 |
| WO | WO-93/09191 A1 | 5/1993 |
| WO | WO-93/10218 A1 | 5/1993 |
| WO | WO-93/11230 A1 | 6/1993 |
| WO | WO-93/25234 A1 | 12/1993 |
| WO | WO-93/25698 A1 | 12/1993 |
| WO | WO-94/03622 A1 | 2/1994 |
| WO | WO-94/26914 A1 | 11/1994 |
| WO | WO-95/13365 A1 | 5/1995 |
| WO | WO-99/45923 A1 | 9/1999 |
| WO | WO-99/47136 A1 | 9/1999 |
| WO | WO-00/54759 A2 | 9/2000 |
| WO | WO-01/15676 A2 | 3/2001 |
| WO | WO-02/080952 A2 | 10/2002 |
| WO | WO-2004/019884 A2 | 3/2004 |
| WO | WO-2005/005453 A2 | 1/2005 |
| WO | WO-2005/005453 A3 | 1/2005 |
| WO | WO-2005/020928 A2 | 3/2005 |
| WO | WO-2005/028616 A2 | 3/2005 |
| WO | WO-2005/123757 A1 | 12/2005 |
| WO | WO-2006/012902 A2 | 2/2006 |
| WO | WO-2006/110490 A2 | 10/2006 |
| WO | WO-2007/028101 A2 | 3/2007 |
| WO | WO-2007/098281 A2 | 8/2007 |
| WO | WO-2008/011071 A2 | 1/2008 |
| WO | WO-2008/041003 A2 | 4/2008 |
| WO | WO-2008/082520 A2 | 7/2008 |
| WO | WO-2008/103951 A1 | 8/2008 |
| WO | WO-2008/109780 A1 | 9/2008 |
| WO | WO-2008/115469 A2 | 9/2008 |
| WO | WO-2009/073186 A1 | 6/2009 |
| WO | WO-2011/006087 A1 | 1/2011 |
| WO | WO-2011/103175 A2 | 8/2011 |
| WO | WO-2012/024581 A2 | 2/2012 |
| WO | WO-2012/024583 A2 | 2/2012 |
| WO | WO-2012/024584 A2 | 2/2012 |
| WO | WO-2013/169397 A1 | 11/2013 |
| WO | WO-2013/169399 A1 | 11/2013 |
| WO | WO-2014/179756 A1 | 11/2014 |
| WO | WO-2015/168636 A1 | 11/2015 |
| ZA | 6808005 | 6/1969 |

OTHER PUBLICATIONS

Abe et al., "Effects of bisphosphonates on osteoclastogenesis in RAW264.7 cells," 2012, *International Journal of Molecular Medicine* 29.6: 1007-1015.

(56) References Cited

OTHER PUBLICATIONS

Acsadi et al., "Human dystrophin expression in mdx mice after intramuscular injection of DNA constructs," 1991, Nature 352: 815-818.
Aghaloo et al., "Oxysterols enhance osteoblast differentiation in vitro and bone healing in vivo," 2007, Journal of Orthopaedic Research 25(11):1488-1497 (also known as Aghaloo 2006 in press).
Akazawa et al., "The upregulated expression of sonic hedgehog in motor neurons after rat facial nerve axotomy," 2004, Journal of Neuroscience, 24(36):7923-7930.
Albers M. et al., "A novel principle for partial agonism of liver X receptor ligands," 2006, Journal of Biological Chemistry 281(8):4920-4930.
Albrektsson et al., "Osteoinduction, osteoconduction and osseointegration," 2001, European Spine Journal, 10:S96-S101.
Almeida et al., "Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT," 2005, Journal of Biological Chemistry 280(50):41342-41351.
Amantea et al. "Oxysterols are novel activators of hedgehog and Wnt signaling," 2006, Journal of Bone and Mineral Research 21:S157-S157.
Amantea et al., "Oxysterol-induced osteogenic differentiation of marrow stromal cells is regulated by Dkk-1 inhibitable and P13-Kinase mediated signaling," 2008, Journal of Cellular Biochemistry 105(2): 424-436.
Antonio et al. "Oxysterol and 9-cis-retinoic acid stimulate the group IIA secretory phospholipase A2 gene in rat smooth-muscle cells," 2003, Biochemical Journal, 376(2): 351-360.
Arns et al., "Design and synthesis of novel bone-targeting dual-action pro-drugs for the teament and reversal of osteoporosis," 2012, Bioorganic and Medicinal Chemistry. 20(6):2131-2140.
Arnsdorf et al., "The periosteum as a cellular source for functional tissue engineering," 2009, Tissue Engineering 15(9):2637-2642.
Aspray et al., "Treatment of osteoporosis in women intolerant of oral bisphosphonates," 2012, Maturitas, 71:76-78.
Ayukawa et al., "Local application of statin promotes bone repair through the suppression of osteoclasts and the enhancement of osteoblasts at bone-healing sites in rats," 2009, Oral Surgary, Oral Medicine, Oral Pathology, Oral Radiology, and Endodontics 107(3): 336-342.
Bailey et al., "Sonic Hedgehog paracrine signaling regulates metastasis and lymphangiogenesis in pancreatic cancer," 2009, Oncogene 28(40): 3513-3525.
Banerjee et al., "Runt homology domain proteins in osteoblast differentiation: AML3/CBFA1 is a major component of a bone-specific complex," 1997, Journal of Cellular Biochemistry 66(1):1-8.
Bannai et al., "Studies on steroids. Part 37. Synthesis of the four stereoisomers of 20,22-epoxycholesterol," 1976, Journal of the Chemical Society, Perkin Transactions 1 (19): 2116-2120.
Barginear et al., "The hedgehog pathway as a therapeutic target for treatment of breast cancer," 2009, Breast cancer research and treatment 116(2):239-246.
Basu et al., "Association between oxidative stress and bone mineral density," 2001, Biochemical and Biophysical Research Communications 288(1):275-9.
Bauss et al., "Effect of 17B-estradiol-biphosphonate conjugates, potentiial bone-seeking estrogen pro-drugs, on 17B-estradiol serum kinetics and bone mass in rats," 1996, Calcified Tissue International 59: 168-173.
Beckers et al., "Disruption of hedgehog signalling in ApoE −/− mice reduces plasma lipid levels, but increases atherosclerosis due to enhanced lipid uptake by macrophages," 2007, Journal of Pathology 212(4):420-428.
Bennett et al., "Regulation of Wnt signaling during adipogenesis," 2002, Journal of Biological Chemistry 277(34): 30998-31004.
Bennett et al., "Regulation of osteoblastogenesis and bone mass by Wnt10b," 2005, Proceedings of the National Academy of Sciences of the United States of America 102(9):3324-3329.
Bergman et al., "Age-related changes in osteogenic stem cells in mice," 1996, Journal of Bone and Mineral Research 11:568-577.
Bestmann et al., "Synthesis and reaction of diazoacetyl chloride-Detection of Diazoketene," 1979, Angewandte Chemie International Edition in English 18(12):947-948.
Bijlsma et al., "Hedgehog: an unusual signal transducer," 2004, Bioessays 26(4):387-394.
Bijlsma et al., "Hedgehog morphogen in cardiovascular disease," 2006, Circulation 114(18):1985-1991.
Bilezikian et al., "Therapy of male osteoporosis with parathyroid hormone," 2001, Calcified Tissue International 69(4):248-251.
Bjorkhem et al., "On the possible use of the serum level of 7a-hydroxycholesterol as a marker for incrased activity of the cholesterol 7a-hydroxylase in humans," 1987, jJournal of Lipid Research 28(8): 889-894.
Bjorkhem et al., "Oxysterols in human circulation: which role do they have?," 2002, Current opinions in lipidology 13(3):247-253.
Bjorkhem et al., "Oxysterols: friends, foes, or just fellow passengers?," 2002, Arteriosclerosis, thrombosis, and vascular biology 22(5):734-742.
Black et al., "Continuing bisphosphonate treatment for osteoporosis—for whom and for how long?" 2012, New England Journal of Medicine 366(22), 2051-2053.
Boguslawski et al., "Activation of osteocalcin transcription involves interaction of protein kinase A- and protein kinase C-dependent pathways," 2000, The Journal of Biological Chemistry. 275(2):999-1006.
Boland et al., "Wnt 3a promotes proliferation and suppresses osteogenic differentiation of adult human mesenchymal stem cells," 2004, Journal of Cellular Biochemistry. 93(6):1210-30.
Braunersreuther et al., "Leukocyte recruitment in atherosclerosis: potential targets for therapeutic approaches?" 2006, Cellular and Molecular Life Sciences 63(18): 2079-2088.
Brewer et al., "Current and future treatment options in osteoporosis," 2011, European Journal of Clinical Pharmacology 67(4): 321-331.
Bruice, T. C. et al. Bioorganic Mechanisms, vol. 1, W. A. Benjamin, New York, 1966, 1-258.
Bunta et al., "Stereoselective synthesis of (22R)- and (22S)-castasterone/ponasterone A hybrid compounds and evaluation of their molting hormone activity," 2004, Steroids 69: 483-493.
Burger et al., "Acetylenic cholesteryl derivatives as irreversible inhibitors of ecdysone biosynthesis," 1988, Tetrahedron 44(4): 1141-1152.
Burstein et al., "A Preliminary Report on the Intermediates in the Conversion in Vitro of Cholesterol to Pregnenolone in Adrenal Preparations," 1969, Steroids 14;(2):207-217.
Burstein, et al., "Reactions of 20-Hydroxylated Steroids with Bovine Adrenal Tissue Preparations," 1969, Steroids 13(3):399-412.
Byon et al., "Stereospecific synthesis of the four 20,22-epoxycholesterols and of (Z)-20(22)-Dehydrocholesterol," 1976, The Journal of Organic Chemistry 41:3716-3722.
Byrd et al., "Hedgehog signaling in murine vasculogenesis and angiogenesis," 2004, Trends in cardiovascular medicine 14(8):308-313.
Cadot et al., "First synthesis of a steroid containing an unstable 19-nor-androsta-1,5-dien-3-one system," 2006, Tetrahedron 62: 4384-4392.
Canalis, "Update in new anabolic therapies for osteoporosis," 2010, The Journal of Clinical Endocrinology and Metabolism 95(4), 1496-1504.
Caplan, "The mesengenic process," 2004, Bone Repair and Regeneration 21(3):429-435.
Caplan et al., "Mesenchymal stem cells: building blocks for molecular medicine in the 21st century," 2001, Trends in Molecular Medicine 7(6):259-64. Review.
Chan et al. "Age-related bone loss: old bone, new facts," 2002, Gerontology 48(2):62-71.

(56) References Cited

OTHER PUBLICATIONS

Chaudhuri et al., "Stereochemistry of the addition reactions of Grignard reagents to 20-keto steroids. Syntheses of 17alpha,20alpha-dihydroxycholesterol," 1969, *The Journal of Organice Chemistry* 34(12):3759-3766.
Chen et al., "Inhibition of hedgehog signaling by direct binding of cyclopamine to Smoothened," 2002, *Genes & Development* 16(21):2743-2748.
Chen et al., "Age-related osteoporosis in biglycan-deficient mice is related to defects in bone marrow stromal cells," 2002, *Journal of Bone and Mineral Research* 17(2):331-340.
Chen et al., "Bone morphogenetic proteins." 2004, *Growth Factors* 22(4):233-41.
Cheng et al., "Chemistry and Biochemistry of Chinese Drugs. Part 1. Sterol Derivatives Cytotoxic to Hepatoma Cells, Isolated from the Drug Bombyx cum Botryte," 1977, *Journal of Chemical Research* (S), v. 9 p. 217.
Chisholm et al., "The LXR ligand T0901317 induces severe lipogenesis in the db/db diabetic mouse," 2003, *Journal of Lipid Research* 44(11):2039-2048; 2003.
Choo et al., "Cytochrome P-450 inhibition blocks bone resorption in vitro and in vivo," 1999, *Otolaryngology—Head and Neck Surgery*, 120(1): 84-91.
Chuu et al., "The liver X receptor agonist T0901317 acts as androgen receptor antagonist in human prostate cancer cells," 2007, *Biochemical and biophysical research communications* 357(2):341-346.
Chuu et al., "Inhibition of tumor growth and progression of LNCaP prostate cancer cells in athymic mice by androgen and liver X receptor agonist," 2006, *Cancer Research* 66(13):6482-6486.
Ciobanu et al., "Synthesis and steroid sulphatase inhibitory activity of C19- and C21-steroidal derivatives bearing a benzyl-inhibiting group," 2001, *European Journal of Medicinal Chemistry* 36(7), pp. 659-671.
Clement-Lacroix et al., "Lrp5-independent activation of Wnt signaling by lithium chloride increases bone formation and bone mass in mice," 2005, *Proceedings of the National Academy of Sciences of the United States of America* 102(48):17406-17411.
Clevers H., "Wnt/beta-catenin signaling in development and disease," 2006, *Cell* 127(3):469-80.
Cline et al., "Perspectives for gene therapy: inserting new genetic information into mammalian cells by physical techniques and viral vectors," 1985, *Pharmacology and therapeutics* 29(1):69-92.
Cohen, "The hedgehog signaling network," 2003, *American Journal of Medical Genetics* 123A:5-28.
Corcoran et al., "Oxysterols stimulate sonic hedgehog and proliferation of medulloblastoma cells," 2006, *Proceedings of the National Academy of Sciences* 103(22): 8408-8413.
Cosman. "Anabolic and Atiresorptive Therapy for Osteoporosis: Combination and Sequential Approaches," 2014, *Current osteoporosis reports* 12(4):385-395.
Cummings et al., "Epidemiology and outcomes of osteoporotic fractures," 2002, *The Lancet* 359(9319):1761-1767.
Day et al., "Wnt/beta-catenin signaling in mesenchymal progenitors controls osteoblast and chondrocyte differentiation during vertebrate skeletogenesis," 2005,*Developmental Cell*. 8(5):739-50.
De La Rosa et al., "Cross-coupling reactions of monosubstituted acetylenes and aryl halides catalyzed by palladium on charcoal," 1990, *Synthetic Communications* 20(13): 2059-2064.
Debiais et al., "Fibroblast growth factor-2 induces osteoblast survival through a phosphatidylinositol 3-kinase-dependent, -beta-catenin-independent signaling pathway," 2004, *Experimental Cell Research* 297(1):235-46.
Devos et al., "Syntheseis of acyl halides under very mild conditions," 1979, *Journal of the Chemical Society, Chemical Communications* 24:1180-1181.
Dimitriou et al., "Bone regeneration: current concepts and future directions," 2011, *BMC Medicine* 9(1):1-10.

Dimmeler et al. "HMG-CoA reductase inhibitors (statins) increase endothelial progenitor cells via the PI 3-kinase/Akt pathway," 2001, *Journal of Clin Invest.* 108(3): 391-397.
Dlugosz et al., "Following the Hedgehog to new cancer therapies," 2009, *New England Journal of Medicine* 361(12):1202-1205.
Drew et al., "Synthesis of Pregnenolone of Flourescent Cholesterol Analogue Probes with Conjugated Unsaturation in the Side Chain," 1987, *Journal of Organic Chemistry* 52(18):4047-4052.
Ducy et al., "Osf2/Cbfa1: A transcriptional activator of osteoblast differentiation," 1997, *Cell* 89(5):747-754.
Ducy, "Cbfa1: a molecular switch in osteoblast biology," 2000, *Developmental Dynamics* 219(4):461-71.
Dwyer et al., "Oxysterols are novel activators of the Hedgehog signaling pathway in pluripotent mesenchymal cells," 2007, *The Journal of Biological Chemistry* 282(12):8959-8968.
Eastell, "Treatment of postmenopausal osteoporosis," 1998, *The New England Journal of Medicine* 338(11):736-746.
Ebetino et al., "The relationship between the chemistry and biological activity of the bisphosphonates," 2011, *Bone* 49(1):20-33.
Edwards et al., "Sterols and isoprenoids: signaling molecules derived from the cholesterol biosynthetic pathway," 1999, *Annual review of biochemistry* 68(1):157-185.
Edwards et al., "BAREing it all: the adoption of LXR and FXR and their roles in lipid metabolism," 2002, *Journal of lipid research* 43(1):2-12.
Ettinger, "Aging bone and osteoporosis: strategies for preventing fractures in the elderly," 2003, *Archives of Internal Medicine* 163(18):2237-2246.
Fajas et al., "Regulation of peroxisome proliferator-activated receptor gamma expression by adipocyte differentiation and determination factor 1/sterol regulatory element binding protein 1: implications for adipocyte differentiation and metabolism," 1999, *Molecular and Cellular Biology* 19(8):5495-5503.
Feldmann et al., "Blockade of Hedgehog signaling inhibits pancreatic cancer invasion and metastasis: A new paradigm for combination therapy in solid tumors," 2007, *Cancer Research* 67(5):2187-2196.
Fievet et al., "Liver X receptor modulators: Effects on lipid metabolism and potential use in the treatment of atherosclerosis," 2009, *Biochemical Pharmacology* 77(8):1316-1327.
Forman et al., "The orphan nuclear receptor LXRa is positively and negatively regulated by distinct products of mevalonate metabolism," 1997, *Proceedings of the National Academy of Sciences of the United States of America* 94(20), pp. 10588-10593.
Franceschi et al., "Gene Therapy for Bone Formation: In Vitro and In Vivo Osteogenic Activity of an Adenovirus Expressing BMP7," 2000, *Journal of Cellular Biochemistry* 78:476-486.
Franceschi et al., "Regulation of the Osteoblast-Specific Transcription Factor, Runx2: Responsiveness to Multiple Signal Transduction Pathways," 2003, *Journal of Cellular Biochemistry* 88(3):446-454.
Friedmann et al., "Progress toward human gene therapy," 1989, *Science* 244(4910):1275-1281.
Fujita et al., "Runx2 induces osteoblast and chondrocyte differentiation and enchances their migration by coupling with PI3K-Akt signaling," 2004, *The Journal of Cell Biology* 166(1):85-95.
Fukuchi et al., "Antiproliferative effect of liver x receptor agonists on LNCaP prostate cancer cells," 2004, *Cancer Research* 64(21): 7686-7689.
Galus et al., "Fluvastatin does not elevate periosteal osteogenesis induced by Moloney sarcoma virus (MSV) in mice," 2006, *Pharmacological Reports* 58(1):60.
Garrett et al., "Selective inhibitors of the osteoblast protease stimulate bone formation in vivo and in vitro," 2003, *The journal of clinical investigation* 111(11):1771-1782.
Gaur et al., "Canonical WNT signaling promotes osteogenesis by directly stimulating *Runx2* gene expression," 2005, *The Journal of Biological Chemistry* 280(39): 33132-33140.
Gen et al., "Nonenzymic biogenetic-like olefinic cyclizations. Stereospecific cyclization of dienic acetals," 1973, *Journal of the American Chemical Society* 95(8):2656-2663.
Geyeregger et al., "Liver x receptors interfere with cytokine-induced proliferation and cell survival in normal and leukemic lymphocytes," 2009, *Journal of Leukocyte Biology* 86:1039-1048.

(56) References Cited

OTHER PUBLICATIONS

Ghosh-Choudhury et al., "Requirement of BMP-2-induced phosphatidylinositol 3-kinase serine/threonine kinase in osteoblast differentiation and Smad-dependent *BMP-2* gene transcription," 2002, *Journal of Biological Chemistry* 277(36):33361-33368.

Ghosh-Choudhury et al., "Statin-induced Ras activation integrates the phosphatidylinositol 3-kinase signal to akt and mapk for bone morphogenetic protein-2 expression in osteoblast differentiaiton," 2007, *The Journal of Biological Chemstry* 282(7):4983-4993.

Gill et al., "Sterol regulators of cholesterol homeostasis and beyond: The oxysterol hypothesis revisited and revised," 2008, *Progress in Lipid Research* 47(6):391-404.

Gimble et al., "Peroxisome proliferator-activated receptor-? activation by thiazolidinediones induces adipogenesis in bone marrow stromal cells," 1996, *Molecular Pharmacology* 50(5):1087-1094.

Goltzman et al., "Discoveries, drugs and skeletal disorders," 2002, *Nature Reviews Drug Discovery* 1(10):784-796.

Gordon et al., "Wnt signaling: multiple pathways, multiple receptors, and multiple transcription factors," 2006, *Journal of Biological Chemisty* 281(32):22429-22433.

Gori et al., "Differentiation of human marrow stromal precursor cells: bone morphogenetic protein-2 increases OSF2/CBFA1, enhances osteoblast commitment, and inhibits late adipocyte maturation," 1999, *Journal of Bone and Mineral Research* 14(9):1522-1535.

Gregorio-King et al., "Effect of oxysterols on hematopoietic progentior cells," 2002, *Experimental Hematology* 30(7): 670-678.

Hanada et al., "Stimulatory effects of basic fibroblast growth factor and bone morphogenetic protein-2 osteogenic differentiation of rat bone marrow-derived mesenchymal stem cells," 1997 *Journal of Bone and Mineral Research* 12(10): 1606-1614.

Hanley et al., "Oxysterols induce differentiation in human keratinocytes and increase AP-1-dependent involucrin transcription," 2000, *Journal of Investigative Dermatology* 114(3):545-553.

Hayden et al., "Induction of moncyte differentiation and foam cell formation in vitro by 7-ketocholesterol," 2002, *Journal of Lipid Research* 43(1):26-35.

Hicok et al., "Development and characterization of conditionally immortalized osteoblast precursor cell lines from human bone marrow stroma," 1998, *Journal of Bone and Mineral Research* 13(2):205-217.

Hill et al., "Canonical Wnt/beta-catenin signaling prevents osteoblasts from differentiating into chondrocytes," 2005, *Developmental Cell* 8(5):727-738.

Hilton M. et al., "Ihh controls cartilage development by antagonizing Gli3, but requires additional effectors to regulate osteoblast and vascular development," 2005, *Development* 132(19):4339-4351.

Hirotsu et al., "Smoothened as a new therapeutic target for human osteosarcoma," 2010, *Molecular Cancer* 9(1):1-14.

Hochman E. et al., "Molecular pathways regulating pro-migratory effects of hedgehog signaling," 2006, *Journal of Biological Chemistry* 281(45):33860-33870.

Hokugo et al., "A novel oxysterol promotes bone regenration in rabbit cranial bone defects," 2013, *Journal of Tissue Engingeering and Regenerative Medicine*.

Honda et al., "Structures of thornasterols A and B (Biologically active glycosides from Asteroidia, XI)," 1986, *Tetrahedron Letters* 27(29):3369-3372.

Honda et al., "Stereoselective synthesis of petrosterol and a formal synthesis of aragusterols," 1996, *Journal of the Chemical Society, Perkin Transactions 1* 18: 2291-2296.

Hosack et al., "Identifying biological themes within lists of genes with EASE," 2003, *Genome Biology* 4(10):R70.

Hu et al., "Sequential roles of hedgehog and Wnt signaling in osteoblast development," 2004, *Development* 132(1):49-60.

Hummasti et al., "Liver X receptors are regulators of adipocyte gene expression but not differentiation: identification of apoD as a direct target," 2004, *Journal of Lipid Research* 45(4):616-625.

Ichioka et al., Prevention of senile osteoporosis in SAMP6 mice by intrabone marrow injection of allogeneic bone marrow cells, 2002, *Stem Cells* 20(6):542-51.

International Search Report and Written Opinion issued in PCT/US2015/028917 dated Jul. 27, 2015.

International Search Report and Written Opinion issued in PCT/US2014/036680 dated Sep. 10, 2014.

International Search Report and Written Opinion issued in PCT/US2008/003493 dated Oct. 12, 2009.

International Search Report and Written Opinion issued in PCT/US2010/041560 dated Aug. 31, 2010.

International Search Report and Written Opinion issued in PCT/US2013/032650 dated Jul. 18, 2013.

International Search Report and Written Opinion issued in PCT/US2013/039748 dated Sep. 25, 2013.

International Search Report and Written Opinion issued in PCT/US03/027105 mailed May 5, 2004.

International Search Report and Written Opinion issued in PCT/US04/028162 mailed Feb. 22, 2005.

International Search Report and Written Opinion issued in PCT/US05/19870 mailed Oct. 14, 2005.

International Search Report and Written Opinion issued in PCT/US06/012902 mailed Jul. 7, 2008.

International Search Report and Written Opinion issued in PCT/US06/34374 mailed Jun. 16, 2008.

International Search Report and Written Opinion issued in PCT/US07/016309 mailed Sep. 16, 2008.

International Search Report and Written Opinion issued in PCT/US07/05073 mailed Oct. 29, 2007.

International Search Report and Written Opinion issued in PCT/US07/25833 mailed Sep. 11, 2008.

International Search Report and Written Opinion issued in PCT/US08/013319 mailed Apr. 8, 2009.

International Search Report and Written Opinion issued in PCT/US2011/025064 mailed Nov. 9, 2011.

Iwata et al., "Demineralized bone matrix and native bone morphogenetic protein in orthopaedic surgery," 2002, *Clinical Orthopaedics and Related Research* 395:99-109.

Izumo et al., "Lipophilic statins can be osteogenic by promoting osteoblastic calcification in a Cbfa1- and BMP-2-independent manner," 2001, *Methods and Findings in Experimental and Clinical Pharmacology* 23(7): 389-394.

Jahnke et al., "An in vitro Assay to Measure Targeted Drug Delivery to Bone Mineral," 2010, *ChemMedChem* 5(5):770-776.

Jiang et al., "Hedgehog signaling in development and cancer". 2008, *Developmental Cell* 15(6):801-812.

Johnson et al., "Novel oxysteols have pro-osteogenic and anti-adipogenic effects in vitro and induce spinal fusion in vivo," 2011, *Journal of Cellular Biochemistry* 112(6): 1673-1684.

Johnson et al., "LRP5 and Wnt signaling: a union made for bone," 2004, *Journal of Bone and Mineral Research* 19(11):1749-57.

Johnson et al., "Human bone morphogenetic protein allografting for reconstruction of femoral nonunion," 2000, *Clinical Orthopaedics and Related Research* 371:61-74.

Joseph S., et al., "Synthetic LXR ligand inhibits the development of atherosclerosis in mice," 2002, *Proceedings of the National Academy of Sciences* 99(11):7604-7609.

Jung et al., "First total synthesis of Zestobergesterol A and active structural analogues of the Xestobergesterols1," 1999, *Organic Letters* 1(10):1671-1674.

Juvet et al., "On the role of liver X receptors in lipid accumulation in adipocytes," 2003, *Molecular Endocrinology* 17(2):172-82.

Kadiyala et al., "Culture expanded canine mesenchymal stem cells possess osteochondrogenic potential in vivo and in vitro," 1997, *Cell Transplantation*, 6(2):125-134.

Kametani et al., "Stereocontrolled synthesis of 2-deoxycrustecdysone and related compounds," 1986, *The Journal of Organic Chemistry* 51(15):2932-2939.

Kaneko et al., "Induction of Intestinal ATP-binding cassette transporters by a phytosterol-derived liver x receptor agonist," 2003, *The Journal of Biological Chemistry* 278(38)36091-36098.

(56) References Cited

OTHER PUBLICATIONS

Kennell et al., "Wnt signaling inhibits adipogenesis through beta-catenin-dependent and -independent mechanisms," 2005, *Journal of Biological Chemistry* 280(25):24004-24010.
Kha et al., "Oxysterols regulate differentiation of mesenchymal stem cells: pro-bone and anti-fat," 2004, *Journal of Bone and Mineral Research* 19(5):830-840.
Kim et al., "Hedgehog signaing and osteogenic differentiation in multioptent bone marrow stromal cells are inhibited by oxidative stress," 2010, *Journal of Biological Chemistry* 111(5):1199-1209.
Kim et al., "ADD1/SREBP1 activates PPARgamma through the production of endogenous ligand," 1998, *Proceedings of the National Academy of Sciences* 95(8):4333-4337.
Kim et al., "Osteogenic oxysterol, 20(S)-Hydroxycholesterol, inhibits PPAR gamma expression and adipogenic differentiation of bone marrow stromal cells through a hedgehog-, wnt-, and MAPK-Dependent Mechanism," 2006, *Journal of Bone and Mineral Research* 21(1): S394.
Kim et al., "20(5)-hydroxycholesterol inhibits PPARgamma expression and adipogenic differentiation of bone marrow stromal cells through a Hedgehog-dependent mechanism," 2007, *Journal of Bone and Mineral Research* 22(11):1711-9.
Kim et al., "Identification of Two Brassinosteroids from the Cambial Region of Scots Pine (*Pinus silverstris*) by Gas Chromatography-Mass Spectometry, after Detection Using a Dwarf Rice Lamina Incilnation Bioassay," 1990, *Plant Physiology* 94(4):1709-1713.
Kim et al., "Osteogenic oxysterol, 20(S)-hydroxycholesterol, induces Notch target gene expression in bone marrow stromal cells," 2010, *Journal of Bone and Mineral Research* 25(4):782-795.
Komori et al., "Regulation of skeletal development by the Runx family of transcription factors," 2005, *Journal of Cellular Biochemistry* 95(3):445-453.
Koreeda et al., "Chirality transfer in stereoselective synthesis. A highly stereocontrolled synthesis of 22-hydroxylated steroid side chains via the [2,3]-Wittig rearrangmeent," 1986, *Journal of Organic Chemistry* 51(21):4090-4092.
Kurland et al., "Parathyroid hormone as a therapy for idiopathic osteoporosis in men: effects on bone mineral density and bone markers" 2000, *Journal of Clinical Endocrinology and Metabolism* 85(9):3069-3076.
Larsson et al. "Kinetics of GI progression in 3T6 and SV-3T3 cells following treatment by 25-hydroxycholesterol." 1986, *Cancer Research* 46(3):1233-1238.
Lefevre et al., "Adrenal cholesterol-binding protein: properties and partial purification," 1978, *FEBS Letters* 89(2): 287-292.
Lehmann et al., "Activation of the nuclear receptor LXR by oxysterols defines a new hormone response pathway," 1997, *Journal of Biological Chemistry* 272(6):3137-3140.
Li et al., "Delivering on the promise of bone morphogenetic proteins," 2001, *Trends in Biotechnology* 19(7):255-65.
Liao X. et al., "Aberrant activation of hedgehog signaling pathway in ovarian cancers: effect on prognosis, cell invasion and differentiation," 2009, *Carcinogenesis* 30(1):131-140.
Libby et al., "Inflammation in atherosclerosis," 2002, *Nature* 420:868-874.
Lieberman et al., "The role of growth factors in the repair of bone," 2002, *Journal of Bone and Joint Surgery* 84A(6):1032-1044.
Lin, "Bisphosphonates: A review of their pharmacokinetic properties," 1996, *Bone* 18(2):75-85.
Lin et al., "Pharmacokinetics of alendronate: an overview," 1999, *International journal of clinical practice. Supplement* 101:18-26.
Liu et al., "Interferon-inducible cholesterol-25-hydroxylase broadly inhibits viral entry by production of 25-hydroxycholesterol," 2013, *Immunity* vol. 38, pp. 92-105.
Liu et al., "The effect of simvastatin on the differentiation of marrow stromal cells from aging rats," 2009, *Die Pharmazie—An International Journal of Pharmaceutical Sciences* 64(1), pp. 43-48.
Long et al., "Genetic manipulation of hedgehog signaling in the endochondral skeleton reveals a direct role in the regulation of chondrocyte proliferation," 2001, *Development* 128(24):5099-5108.
Luhmann et al., "Bone targeting for the treatment of osteoporosis," 2012, *Journal of Controlled Release* 161(2):198-213.
Lum et al., "The hedgehog response network: sensors, switches, and routers," 2004, *Science* 304(5678):1755-1759.
Lyritis et al., "Bone anabolic versus bone anticatabolic treatment of postmenopausl osteoporosis," 2010, Annals of the New York Academy of Sciences 1205:277-283.
Maeda et al., "Simvastatin promotes osteoblast differentiation and mineralization in MC3T3-E1 cells," 2001, *Biochemical and Biophysical Research Communications* 280(3):874-877.
Maggio et al., "Marked decrease in plasma antioxidants in aged osteoporotic women: results of a cross-sectional study," 2003, *Journal of Clinical Endocrinology and Metabolism* 88(4):1523-1527.
Majors et al., "Characterization of human bone marrow stromal cells with respect to osteoblastic differentiation," 1997, *Journal of Bone and Joint Surgery* 15(4):546-557.
Makino et al., "Steroid conformations in solid and solution: stereoselectivity of Grignard addition to 20-keto steroids," 1978, *Journal of Organic Chemistry* 43(2): 276-280.
Manolagas et al., "Birth and death of bone cells: basic regulatory mechanisms and implications for the pathogenesis and treatment of osteoporosis," 2000, *Endocrine Reviews* 21(2):115-137.
Manolagas et al., "Cellular and molecular mechanisms of osteoporosis," 1998, *Aging Clinical and Experimental Research* 10(3):182-190.
Mazzocchi et al., "Photochemical additions of alkenes to phthalimides. Mechanistic investigation on the stereochemistry of alkene additions and the effect of aryl substituents on the regiochemistry of alkene additions," 1983, *Journal of Organic Chemistry* 48(18): 2981-2989.
Mbalaviele et al., "Beta-catenin and BMP-2 synergize to promote osteoblast differentiation and new bone formation," 2005, *Journal of Cellular Biochemistry* 94(2):403-418.
Meaney et al., "Evidence that the major oxysterols in human circulation originate from distinct pools of cholesterol: a stable isotope study," 2001, *Journal of Lipid Research* 42(1):70-78.
Melton et al., "How many women have osteoporosis now?," 1995, *Journal of Bone and Mineral Research* 10(2):175-177.
Meunier et al., "Osteoporosis and the replacement of cell populations of the marrow by adipose tissue: A quantitative study of 84 iliac bone biopsies," 1971, *Clinical Orthopedics and Related Research* 80:147-154.
Mezey et al. "Dispersed donor salivary gland cells are widely distributed in the recipient gland when infused up the ductal tree," 2009, *Biotechnic and Histochemistry* 84(6):253-260.
Mimaki et al., "Lipid and steroidal constituents of *Lilium auratum* var. *platyphyllum* and *L. tenuifolium*," 1989, *Phytochemistry* 28(12), 3453-3458.
Mitsunobu O., "The use of diethyl azodicarboxylate and triphenylphosphine in syntheses and transformation of natural products," 1981, *Synthesis* 01:1-28.
Miyamoto et al., "Prostaglandin E2-mediated anabolic effect of a novel inhibitor of phosphodiesterase 4, XT-611, in the in vitro bone marrow culture," 2003, *Journal of Bone and Mineral Research* 18(8):1471-1477.
Mody et al., "Oxidative stress modulates osteoblastic differentiation of vascular and bone cells," 2001, *Free Radical Biology and Medicine* 31(4):509-519.
Moerman et al., "Aging activates adipogenic and suppresses osteogenic programs in mesenchymal marrow stroma/stem cells: the role of PPAR-gamma2 transcription factor and TGF-beta/BMP signaling pathways," 2004, *Aging Cell* 3(6):379-89.
Montgomery et al., "A Novel Osteogenic Oxysterol Compound for Therapeutic Development to Promote Bone Growth: Activation of Hedgehog Signaling and Osteogenesis through Smoothened Binding," 2014, *Journal of Bone and Mineral Research* 29(8):1872-1885).
Morioka et al., "Design, synthesis and biological evaluation of novel estradio-biphosphonate conjugates as bone-specific estrogens," 2010, Bioorganic and Medicinal Chemistry 18(3):1143-1148.

(56) References Cited

OTHER PUBLICATIONS

Morisaki et al., "Studies on steroids. XLV. Synthesis of the four stereoisomers of 20,22-dihydroxycholesterol," 1977, *Chemical andPharmaceutical Bulletin* 25(10):2576-2583.

Morisaki et al., "Stereochemical specificity at carbon-20 and -22 of hydroxylated cholsterals for side-chain cleavage by adrenocortical cytochrome P-450sec," 1976, *FEBS Letters* 72(2):337-40.

Mullor et al., "Wnt signals are targets and mediators of Gli function," 2001, *Current Biology* 11(10):769-73.

Mullor et al., "Pathways and consequences: hedgehog signaling in human disease," 2002, *Trends in Cell Biology* 12(12):562-569.

Mundy et al., "Stimulation of bone formation in vitro and in rodents by statins," 1999, *Science* 286(5446):1946-1949.

Mundy et al., "Directions of drug discovery in osteoporosis," 2002, *Annual Review of Medicine* 53(1):337-354.

Muschitz et al., "Antiesorptives overlapping ongoing teriparatide treatment result in additional increases in bone mineral density," 2013, *Journal of Bone and Mineral Research* 28(1):196-205.

Myers et al., "Hedgehog pathway modulation by multiple lipid binding sites on the smoothened effector of signal response," 2013, *Developmental Cell* 26(4):346-357.

Nachtergaele et al., "Oxysterols are allosteric activators of the oncoprotein Smoothened," 2012, *Nature Chemical Biology* 8(2):211-220.

Nachtergaele et al., "Structure and function of the Smoothened extracellular domain in vertebrate Hedgehog signaling," 2013, *eLife* 2:e01340.

Nagahisa et al., "Acetylenic mechanism-based inhibitors of cholesterol side chain cleavage by cytochrome P-450scc," 1983, *Journal of Biological Chemistry* 258(11):6721-6723.

Nagano et al., "Chemistry and biochemistry of Chinese drugs, Part II—Hydroxylated sterols, cytotoxic towards cancerous cells: synthesis and testing," 1977, *Journal of Chemical Research (Suppl.)* 218.

Nakamura et al., "Stimulation of bone formation by intraosseous application of recombinant basic fibroblast growth factor in normal and ovariectomized rabbits," 1997, *Journal of Orthopaedic Research* 15(2):307-313.

Nasim et al., "3-O-Phosphate ester conjugates of 17-beta-O-1,3,5(10)-estratriene as novel bone-targeting agents," 2010, *Bioorganic and Medicinal Chemistry Letters* 20:7450-7453.

Nedelcu et al., "Oxysterol binding to the extracellular domain of Smoothened in Hedgehod signaling," 2013, *Nature chemical biology* 9(9):557-564.

Nelson et al., "The oxysterol, 27-hydroxycholesterol, links cholesterol metabolism to bone homeostasis through its actions on the estrogen and liver x receptors," 2011, *Endocrinology* 152(12):4691-4705.

Nickolson et al., "Stereospecific synthesis of (20S,22R)-17α,20,22-trihydroxycholesterol and (20S,22S)-17a,20,22-trihydroxycholesterol," 1972, *Journal of Organic Chemistry* 37(13), 2119-2127.

Nishio et al., "3-hydroxy-3-methylglutaryl coenzyme A reductase inhibitor impairs cell differentiation in cultured adipogenic cells (3T3-L1)." 1996, *European Journal of Pharmacology* 301(1):203-206.

Olkkonen et al., "Oxysterols and oxysterol binding proteins: role in lipid metabolism and atherosclerosis," 2004, *Annals of Medicine* 36(8):562-572.

Otto et al., "Cbfa1, a candidate gene for cleidocranial dysplasia syndrome, is essential for osteoblast differentiation and bone development," 1997, *Cell* 89(5):765-771.

Panakova et al., "Lipoprotein particles are required for hedgehog and wingless signaling," 2005, *Nature* 435:58-65.

Parhami et al., "Lipid oxidation products have opposite effects on calcifying vascular cell and bone cell differentiation. A possible explanation for the paradox of arterial calcification in osteoporotic patients," 1997, *Arteriosclerosis, thrombosis, and vascular biology* 17(4):680-687.

Parhami et al., "Role of the cholesterol biosynthetic pathway in osteoblastic differentiation of marrow stromal cells," 2002, *Journal of Bone and Mineral Research* 17(11):1997-2003.

Parish et al., "Side-chain oxysterol regulation of 3-hydroxy-3-methylglutaryl coenzyme A reductase activity," 1995, *Lipids* 30:247-251.

Parish et al., "Regulation of 3-hydroxy-3-methylglutaryl coenzyme A reductase activity by side-chain oxysterols and their derivatives," 1999, *Critical Reviews in Biochemistry & Molecular Biology* 34(4):265-272.

Peacock C. et al., "Hedgehog signaling maintains a tumor stem cell compartment in multiple myeloma," 2007, *Proceedings of the National Academy of Sciences* 104(10):4048-4053.

Peet et al., "The LXRs: a new class of oxysterol receptors," 1998, *Current Opinion in Genetics & Development* 8(5):571-575.

Peng et al., "Antiatherosclerotic effects of a novel synthetic tissue-selective steroidal liver X receptor agonist in low-density lipoprotein receptor-deficient mice," 2008, *Journal of Pharmacology and Experimental Therapeutics* 327(2):332-342.

Pezacki et al., "Transcriptional profiling of the effects of 25-hydroxycholesterol on human hepatocyte metabolism and the antiviral state it conveys against the hepatitis C virus," 2009, *BMC Chemical Biology* 9(2):1-15.

Pikuleva et al., "Putative Helix F Contributes to Regioselectivity of Hydroxylation in Mitochondrial Cytochrome P450 27A1," 2001, *Biochemistry* 40(25):7621-7629.

Pittenger et al., "Multilineage potential of adult human mesenchymal stem cells," 1999, *Science* 284(5411):143-147.

Porter J. et al., "Cholesterol modification of Hedgehog signaling proteins in animal development," 1996, *Science* 274:255-259.

Poza et al., "Synthesis and evaluation of new 6-hydroximinosteroid analogs as cytotoxic agents," 2007, *Bioorganic and Medicinal Chemistry* 15(14):4722-40.

Prockop DJ., "Marrow stromal cells as stem cells for nonhematopoietic tissues," 1997, *Science*, 276:71-74.

Quarto et al., "Bone progenitor cell deficits and the age-associated decline in bone repair capacity," 1995, *Calcified Tissue International* 56(2):123-129.

Rachner et al., "New Horizons in Osteoporosis," 2011, *Lancet* 377(9773):1276-1287.

Raghow et al., "SREBPs: the crossroads of physiological and pathological lipid homeostasis," 2008, *Trends in Endocrinology and Metabolism* 19(2):65-73.

Raisz LG., "The osteoporosis revolution," 1997, *Annals of Internal Medicine* 126(6):458-462.

Raisz et al., "Pathgenesis of osteoporosis: concepts, conflicts, and prospects," 2005, *Journal of Clinical Investigation* 115(12):3318-3325.

Rao AS., (1991) Addition reactions with formation of carbon-oxygen bones: (1) General methods of epoxidation. Comprehensive Organic Synthesis, Pergamon Press, Eds. Trost BM, Fleming I. 7 (chapter 3.1); 376-380.

Rao et al., "Lovastatin-mediated G1 arrest is through inhibition of the proteosome, independent of hydroxymethyl glutarl-CoA reductase," 1999, *Proc. Natl. Acad. Sci.* 96: 7797-7802.

Rawadi et al., "BMP-2 controls alkaline phosphatase expression and osteoblast mineralization by a Wnt autocrine loop," 2003, *Journal of Bone and Mineral Research* 18(10):1842-53.

Reeve et al., "Treatment with parathyroid peptides and estrogen replacement for severe postmenopausal vertebral osteoporosis: prediction of long-term responses in spine and femu," 2001, *Journal of Bone and Mineral Metabolism* 19:102-114.

Rehman et al., "Antiviral drugs against hepatitus C virus," 2011, *Genetic Vaccines and Therapy* 9(11): 1-10.

Reinholz et al., "Bisphosphonates directly regulate cell proliferation, differentiation, and gene expression in human osteoblasts," 2000, *Cancer Research* 60(21):6001-6007.

Reszka et al., "Mechanism of action of bisphosphonates," 2003, *Current Osteoporosis Reports* 1(2):45-52.

Richardson et al., "Oxysterol-induced osteoblastic differentiation of pluripotent mesenchymal cells is mediated through a PKC-and PKA-dependent pathway," 2007, *Journal of Cellular Biochemistry* 100(5):1131-45.

(56) References Cited

OTHER PUBLICATIONS

Richardson et al. "Characterization of osteogenic oxysterols and their molecular mechanism(s) of action," 2005, *Journal of Bone and Mineral Research* 20(9):S414.
Rickard et al., "Induction of rapid osteoblast differentiation in rat bone marrow stromal cell cultures by dexamethasone and BMP-2," 1994, *Developmental Biology* 161(1):218-28.
Riggs et al., "The prevention and treatment of osteoporosis," 1992, *New England Journal of Medicine* 327(9):620-7.
Riobó et al., "Phosphoinositide 3-kinase and Akt are essential for Sonic Hedgehog signaling," 2006, *Proceedings of the National Academy of Sciences* 103(12):4505-10.
Rodan et al., "Therapeutic approaches to bone diseases," 2000 *Science* 289(5484):1508-1514.
Rodda et al., "Distinct roles for Hedgehog and canonical Wnt signaling in specification, differentiation and maintenance of osteoblast progenitors," 2006, *Development* 133(16):3231-44.
Roodman et al., "Bone Building with bortezomib," 2008, *Journal of Clinical Investigation* 118(2):462-464.
Ruan et al., "An improved synthesis of (20R,22R)-cholest-5-ene-3?,20,22-triol, and intermediate in steroid hormone formation and an activator of nuclear orphan receptor LXR?," 1999, *Steroids* 64(6):385-395.
Rubin, "Southwestern Internal Medical Conference: Treatment considerations in the management of age-related osteoporosis," 1999, *The American Journal of the Medical Sciences*, 318(3):158-170.
Rubin et al., "Targeting the Hedgehog pathway in cancer," 2006, *Nature reviews Drug discovery* 5(12):1026-1033.
Rudin et al., Treatment of medulloblatoma with Hedgehog pathway inhibitor GDC-0449, 2009, *New England Journal of Medicine* 361(12):1173-1178.
Russell, "Oxysterol biosynthetic enzymes," 2000, *Biochimica et Biophysica Acta* 1529:126-135.
Sagan et al., "The influence of cholesterol and lipid metabolism on host cell structure and hepatitis C virus replication," 2006, *Biochemistry and Cell Biology* 84(1):67-79.
Sammons et al., "The role of BMP-6, IL-6, and BMP-4 in mesenchymal stem cell-dependent bone development: effects on osteoblastic differentiation induced by parathyroid hormone and vitamin D3," 2004, *Stem Cells and Development*, 13(3):273-280.
Sanchez et al., "Inhibition of prostate cancer proliferation by interference with SONIC HEDGEHOG-GLI1 signaling," 2004, *Proceedings of the National Academy of Sciences* 101(34):12561-12566.
Sang et al., "Ectopic overexpression of adipogenic transcription factors induces transdifferentiation of MC3T3-E1 osteoblasts," 2005, *Biochemical and Biophysical Research Communications* 327(3): 811-819.
Schaafsma et al. "Delay of natural bone loss by higher intake of specific minerals and vitamins," 2001, *Critical Reviews in Food Science and Nutrition* 41(3):225-249.
Schmidt et al., "A 15-ketosterol is a liver x receptor ligand that suppresses sterol-responsive element binding proteing-2 activity," 2006, *Journal of Lipid Research* 47:1037-1044.
Schroepfer, "Oxysterols: modulators of cholesterol metabolism and other processes," 2000, *Physiological Reviews* 80(1):361-554.
Scott et al., "Comparison of a novel oxsterol molecule and rhBMP2 fusion rates in a rabbit posterolateral lumbar spine model," 2015, *The Spine Journal* 15:733-742.
Semb, "Isozymes of bone esterases," 1970, *Calcified Tissue Research* 6(1):77-80.
Seo et al., "Activated liver X receptors stimulate adipocyte differentiation through induction of peroxisome proliferator-activated receptor gamma expression," 2004, *Molecular and Cellular Biology* 24(8):3430-44.
Shan et al., "Chromatographic behavior of oxygenated derivatives of cholesterol," *Steroids* 68(3):221-233.
Shaw et al., "The Sonic Hedgehog pathway stimulates prostate tumor growth by paracrine signaling and recapitulates embryonic gene expression in tumor myofibroblasts". 2009, *Oncogene* 28(50):4480-4490.
Shea et al., "BMP treatment of C3H10T1/2 mesenchymal stem cells induces both chondrogenesis and osteogenesis," 2003, *Journal of Cellular Biochemistry* 90(6):1112-1127.
Sheikh et al., "Mass spectometry in structural and stereochemical problems. CCXXX Preparation of 5a, 20a and 5a, 17a, 20a-cholestane-3b, 6a-diol. Electron impact induced framentation of steroidal D 17(20), D 20(21) and D 20(22) olefins," 1973, *Journal of Organic Chemistry* 38(20):3545-3553.
Shimaoka et al., "Recombinant growth/differentiation factor-5 (GDF-5) stimulates osteogenic differentiation of marrow mesenchymal stem cells in porous hydroxyapatite ceramic," 2004, *Journal of Biomedical Materials Research Part A* 68(1):168-176.
Shinoda et al., "HMG-CoA Reductase Inhibitor, Acceleration of Bone Formation with Satin," 2000, *Pharmacia* 649-650.
Shouhed et al., "Osteogenic oxysterols inhibit the adverse effects of oxidative stress on osteogenic differentiation of marrow stromal cells," 2005, *Journal of Cellular Biochemistry* 95(6):1276-1283.
Silva et al., "New approaches to the treatment of osteoporosis," 2011, *Annual Review of Medicine* 62:307-322.
Silva-Vargas et al., "Beta-catenin and Hedgehog signal strength can specify number and location of hair follicles in adult epidermis without recruitment of bulge stem cells," 2005, *Developmental Cell* 9(1):121-31.
Sohal et al., "Mechanisms of aging: an appraisal of the oxidative stress hypothesis," 2002, *Free Radical Biology and Medicine* 33(5):575-586.
Song et al., "Effect of simvastatin on bone morphogenetic protein-2 expression and alkaline phosphatase activity of bone marrow stromal cell," 2002, *Chinese Journal of Reparative and Reconstructive Surgery*, 16(6):384-387. Abstract Provided Only.
Sottero et al., "Cholesterol oxidation products and disease: an emerging topic of interest in medicinal chemistry," 2009, *Current Medicinal Chemistry* 16(6):685-705.
Spinella-Jaegle et al., "Sonic hedgehog increases the commitment of pluripotent mesenchymal cells into the osteoblastic lineage and abolishes adipocytic differentiation," 2001, *Journal of Cell Science* 114(11):2085-2094.
Spiro et al., "Spinal fusion with recombinant human growth and differentiation factor-5 combined with a mineralized collagen matrix," 2001, *The Anatomical Record* 263(4):388-395.
Stappenbeck et al., "Novel oxysterols activate the Hedgehod pathway and induce osteogenesis," 2012, *Bioorganic & Medicinal Chemistry Letters*, 22(18): 5893-5897.
Stein et al., "Molecular mechanisms mediating proliferation/differentiation interrelationships during progressive development of the osteoblast phenotype," 1993, *Endocrine Reviews* 14(4):424-442.
Steitz et al., "Smooth Muscle Cell Phenotypic Transition Associated With Calcification: Upregulation of Cbfa1 and Downregulation of Smooth Muscle Lineage Markers," 2001, *Circulation Research* 89:1147-1154.
Stewart et al., "Expression of the developmental Sonic hedgehog (Shh) signalling pathway is up-regulated in chronic lung fibrosis and the Shh receptor patched1 is present in circulating T lymphocytes," 2003, *Journal of Pathology* 199:488-495.
St-Jacques et al., "Indian hedgehog signaling regulates proliferation and differentiation of chondrocytes and is essential for bone formation," 1999, *Genes and Development* 13:2072-2086.
Sugano et al., "Identification of intermediates in the conversion of cholesterol to pregnenolone with a reconstituted cytochrome P-450sec system: accumulation of the intermediate modulated by the adrenodoxin level," 1996, *Journal of Biochemistry* 120(4), pp. 780-787.
Suh et al., "Hedgehog signaling plays a conserved role in inhibiting fat formation," 2006, *Cell Metabolism* 3(1):25-34.
Supplementary European Search Report issued in EP 03749213.9 dated May 14, 2009.
Supplementary European Search Report issued in EP 06824888.9 dated Jun. 24, 2009.

(56) References Cited

OTHER PUBLICATIONS

Swarthout et al., "Parathyroid hormone-dependent signaling pathways regulating genes in bone cells," 2002, *Gene* 282(1-2):1-17.
Sydykov et al., "Synthesis of (20S)-propargyl-5-pregnene-3β,20-diol and its use in the preparation of C27-steroids with an oxidized side chain," 1976, *Bioorganicheskaya Khimiya* 2(11):1531-1537. English Abstract Provided Only.
Sydykov et al, "Partial synthesis of 20(R),22(R)-D 5-cholestene-3b,20,22-triol," 1977, *Izvestiya Akademiii Nauk SSSR, Seriya Khimicheskaya* 1:191-194.
Szendi et al., "1,5-Hydride shift in Wolff-Kishner reduction of (20R)-3?,20, 26-trihydroxy-27-norcholest-5-en-22-one; synthetic, quantum chemical, and NMR studies," 2002, *Steroids* 67:31-38.
Ta et al., "Osteosarcoma treatment: state of the art," 2009, *Cancer Metastasis Reviews* 28(1-2):247-263.
Taipale et al., "The Hedgehog and Wnt signalling pathways in cancer," 2001, *Nature* 411(6835):349-354.
Taylor et al., "24,25-Epoxysterol metabolism in cultured mammalian cells and repression of 3-hydroxy-3-methylglutaryl-CoA reductase," 1986, *Journal of Biological Chemistry* 261(32):15039-15044.
Teplyuk et al., "The osteogenic transcription factor runx2 controls genes involved in sterol/steroid metabolism, including CYP11A1 in osteoblasts,"2009, *Molecular Endocrinology* 23(6):849-861.
Thayer et al., "Hedgehog is an early and late mediator of pancreatic cancer tumorigenesis," 2003, *Nature* 425(6960):851-856.
Thies et al., "Recombinant human bone morphogenetic protein-2 induces osteoblastic differentiation in W-20-17 stromal cells," 1992, *Endocrinology* 130(3):1318-1324.
Tintut et al., "Multilineage Potential of Cells From the Artery Wall," 2003, *Circulation* 108(20):2505-2510.
Väänänen HK., "Mesenchymal stem cells," 2005, *Annals of Medicine* 37(7):469-479.
Valentin-Opran et al., "Clinical evaluation of recombinant human bone morphogenetic protein-2," 2002, *Clinical Orthopaedics and Related Research* 395:110-120.
Vedin et al., "The oxysterol receptor LXR inhibits proliferation of human breast cancer cells," 2009, *Carcinogenesis* 30(4):575-579.
Velgova et al., "On steroids. CXXVI. Further compounds with antisclerotization effect on *Pyrrhocoris apterus* L. larvae: structure and activity correlations," 1969, *Collections of Czechoslovak chemical communications* 34(11): 3354-3376.
Vescini et al., "PTH 1-84: bone rebuilding as a target for the therapy of severe osteoporosis." 2012, *Clinical Cases in Mineral and Bone Metabolism* 9(1):31-36.
Viccica et al., "Role of the cholesterol biosynthetic pathway in osteoblastic differentiation," 2006, *Journal of Endocrinological Investigation* 30(6S): 8-12.
Vine et al., "Dietary oxysterols are incorporated in plasma triglyceride-rich lipoproteins, incrase their susceptibility to oxidation and increase aortic cholesterol concentrations in rabbits," 1998, *Journal of Lipid Research* 38:1995-2004.
Von Hoff et al., "Inhibition of the Hedgehog pathway in advanced basal-cell carcinoma," 2009, *New England Journal of Medicine* 361:1164-1172.
Wada et al., "Calcification of Vascular Smooth Muscle Cell Cultures : Inhibition by Osteopontin," 1999, *Circulation Research* 84:166-178.
Wada et al., "Lack of Positive Correlation Between Statin Ue and Bone Mineral Density in Japanese Subjects With Type 2 Diabetes," 2000, *Archives of Internal Medicine* 160(18):2865.
Wang et al., "Lipid Clearing Agents in Steroid-Induces Osteoporosis," 1995, *Journal of the Formosan Medical Association=Taiwan yi zhi* 94(10): 589-592.
Wang et al., "The pathogenesis and prevention of steroid-induced osteonecrosis," 2000, *Clinical Orthopaedics and Related Research* 370(2000):295-310.
Watanabe et al., "Stereoselective synthesis of (22R)- and (22S)-castasterone/ponasterone A hybrid compounds and evaluation of their molting hormone activity," 2004, *Steroids* 69(7):483-493.

Watson et al., "TGF-beta1 and 25-hydroxycholesterol stimulate osteoblast-like vascular cells to calcify," 1994, *Journal of Clinical Investigation* 93(5):2106-2113.
Westendorf et al., "Wnt signaling in osteoblasts and bone diseases," 2004, *Gene* 341:19-39.
Wiersig et al., "Stereospecific synthesis of the side chain of the steroidal plant sex hormone oogoniol," 1979, *Journal of Organic Chemistry* 44(19):3374-3382.
Wolf et al., "A broad-spectrum antiviral targeting entry of enveloped viruses," 2010, *Proceedings of the National Academy of Sciences* 107(7):3157-3162.
Woo et al., "Enhancement of bone growth by sustained delivery of recombinant human bone morphogenetic protein-2 in a polymeric matrix," 2001, *Pharmaceutical Research* 18(12):1747-1753.
Yamaguchi et al., "Regulation of osteoblast differentiation mediated by bone morphogenetic proteins, hedgehogs, and Cbfa1," 2000, *Endocrine Reviews* 21(4):393-411.
Yamaguchi et al., "Osteoporosis and Vascular Calcfication," 2002, *Clinical Calcium* 39-43. English Abstract Provided Only.
Yang et al., "Transcription factors in bone: developmental and pathological aspects," 2002, *Trends in Molecular Medicine* 8(7):340-5.
Yang et al., "Parathyroid hormone activates PKC-delta and regulates osteoblastic differentiation via a PLC-independent pathway," 2006, *Bone* 38(4):485-96.
Yao et al., "22R-hydroxycholesterol induces differentiation of human nt2 precursor (Ntera2/d1 teratocarcinoma) cells." 2007, *Neuroscience* 148(2):441-453.
Yao et al., "22R-Hydroxycholesterol protects neuronal cells from b-amyloid-induced cytotoxicity by binding β-amyloid peptide," 2002, *Journal of Neurochemistry* 83(5):1110-1119.
Yauch et al., "A paracrine requirement for Hedgehog signaling in cancer," 2008, *Nature* 455(7211):406-410.
O'Toole et al., "Hedgehog overexpression is associated with stromal interactions and predicts for poor outcome in breast cancer," 2011, *Cancer Research* 71(11): 4002-4015.
Yeh et al., "Osteogenic protein-1 (op-1, bmp-7) induces osteoblastic cell differentiation to the pluripotent mesenchymal cell line c2c12," 2002, *Journal of Cell Biochemistry* 87(3): 292-304.
Yoon et al., "Osteoinductive molecules in orthopaedics: basic science and preclinical studies," 2002, *Clinical orthapaedics and related research* 395:33-43.
Yoshida et al., "Core-binding factor beta interacts with Runx2 and is required for skeletal development," 2002, *Nature Genetics* 32(4):633-8.
Yoshida et al., "Stimulation of bone formation and prevention of bone loss by prostaglandin E EP4 receptor activation," 2002, *Proceedings of the National Academy of Sciences* 99(7):4580-5.
Zanchetta et al., "Systematic effects on bone healing of a new hyaluronic acid-like bacterial exopolysaccharide," 2003, *Calcified Tissue International* 73:232-236.
Zander et al., "Chemistry and Biochemistry of Chinese Drugs. Part III. Mechanism of Action of Hydroxylated Sterols on Cultured Hepatoma Cells," 1977, *Journal of Chemical Research* (S)9:219.
Zelcer et al., "Liver X receptors as integrators of metabolic and inflammatory signaling," 2006, *Journal of Clinical Investigation* 116:607-614.
Zhang et al., "Cyclooxygenase-2 regulates mesenchymal cell differentiation into the osteoblast lineage and is critically involved in bone repair," 2002, *Journal of Clinical Investigation* 109(11):1405-1415.
Zhao et al., "E3 ubiquitin ligase Smurf1 mediates core-binding factor alpha1/Runx2 degradation and plays a specific role in osteoblast differentiation," 2003, *Journal of Biological Chemistry* 278(30):27939-44.
Zhao et al., "The zinc finger transcription factor Gli2 mediates bone morphogenetic protein 2 expression in osteoblasts in response to hedgehog signaling," 2006, *Molecular and Cellular Biology* 26(16):6197-6208.
Zimmerman et al., "Stereochemical effects in cyclopropane ring openings: biomimetic ring openings of all isomers of 22, 23-methylenecholesterol acetate," 1984, *Journal of the American Chemical Society* 106(19):5602-5612.

(56) References Cited

OTHER PUBLICATIONS

Ziros et al., "The bone-specific transcriptional regulator Cbfa1 is a target of mechanical signals in osteoblastic cells," 2002, *Journal of Biological Chemistry* 277(26):23934-23941.

Cheng et al., Chemistry and Biochemistry of Chinese Drugs. Part 1. Sterol Derivatives Cytotoxic to Hepatoma Cells, Isolated from the Drug Bombyx cum Botryte, 1977, Journal of Chemical Research (M) v. 9 pp. 2501-2521 (English Abstract only).

Nagano et al., "Chemistry and biochemistry of Chinese drugs, Part II—Hydroxylated sterols, cytotoxic towards cancerous cells: synthesis and testing," 1977, Journal of Chemical Research (M) 2522-2571. (English Abstract only).

Zander et al., "Chemistry and Biochemistry of Chinese Drugs. Part III. Mechanism of Action of Hydroxylated Sterols on Cultured Hepatoma Cells," 1977, Journal of Chemical Research (M)9:2572-2584.

Correa, C. (Jan. 2007). "Guidelines for the Examination of Pharmaceutical Patents: Developing a Public Health Perspective," WHO-ICTSD, UNCTAD, 65 pages.

Guan, Y. et al. (Jul.-Aug. 2000). "Synthesis of compound libraries based on 3,4-diaminocyclopentanol scaffolds," *J Comb Chem* 2(4):297-300.

Neale, J.R. et al. (Feb. 1, 2009, e-published Dec. 24, 2008). "Bone selective effect of an estradiol conjugate with a novel tetracycline-derived bone-targeting agent," *Bioorg Med Chem Lett* 9(3):680-683.

Petrova, N.S. et al. (Mar. 2012, e-published Nov. 10, 2011). "Carrier-free cellular uptake and the gene-silencing activity of the lipophilic siRNAs is strongly affected by the length of the linker between siRNA and lipophilic group," *Nucleic Acid Res* 40(5):2330-2344.

Aghaloo T.L. et al. "Oxysterols enhance osteoblast differentiation in vitro and bone healing in vivo," 2007, *Journal of Orthopaedic Research* (25)11:1488-1497.

Chen et al., "Small molecule modulation of Smoothened activity," 2002, Proceedings of the National Academy of Sciences, 99(22), 14071-14076.

Phelan C. et al., "Selective partial agonism of liver X receptor a is related to differential corepressor recruitement," 2008, Molecular Endocrinology 22(10): 2241-2249.

Schambony A. et al., "Wnt-5A/Ror2 regulate expression of XPAPC through an alternative noncanonical signaling pathway," 2007, Developmental Cell 12(5):779-92.

Shimizu et al., "20?, 22-Dihydroxycholesterol, an Intermediate in the Biosynthesis of Pregnenolone (3?-Hydroxypregn-5-en-20-one) from Cholesterol," 1962, Journal of Biological Chemistry 237(3): 699-702.

Wang et al., "Structure of the human smoothened receptor 7TM bound to an antitumour agent," 2013, Nature 497(7449):338-343.

OXYSTEROL ANALOGUE OXY133 INDUCES OSTEOGENESIS AND HEDGEHOG SIGNALING AND INHIBITS ADIPOGENESIS

CROSS-REFERENCES TO RELATED APPLICATIONS

This application is a U.S. National Stage of International Application No. PCT/US2013/032693, filed on Mar. 15, 2013, which claims the benefit of U.S. Provisional Application No. 61/643,746, filed on May 7, 2012, each of which is incorporated by reference in its entirety.

STATEMENT AS TO RIGHTS TO INVENTIONS MADE UNDER FEDERALLY SPONSORED RESEARCH AND DEVELOPMENT

This invention was made with Government support under AR059794, awarded by the National Institutes of Health. The Government has certain rights in the invention.

BACKGROUND INFORMATION

Biologics are commonly employed to promote bone growth in medical applications including fracture healing and surgical management of spinal disorders (1-4). Spine fusion is often performed by orthopedic surgeons and neurosurgeons alike to address degenerative disc disease and arthritis affecting the lumbar and cervical spine. Historically, autogenous bone graft, commonly taken from the iliac crest of the patient, has been used to augment fusion between vertebral levels. However, the associated donor site morbidity, increased operating time, and increased blood loss associated with harvesting autogenous bone graft (5-7) has provided incentive to find a safe and effective alternative.

Recombinant human bone morphogenetic protein-2 (rhBMP-2) is commonly used to promote spine fusion in humans. Its use was approved in 2002 by the US Food and Drug Administration (FDA) for single-level anterior lumbar interbody fusion (8). The use of rhBMP-2 has increased significantly since this time and indications for its use have expanded to include posterior lumbar spinal fusion as well cervical spine fusion. Despite the efficacy of rhBMP-2, recent reports have called into question its safety when employed during spine fusion surgery. Reported complications have included seroma formation, soft tissue swelling, vertebral osteolysis, ectopic bone formation, retrograde ejaculation, and carcinogenicity (9-12). Moreover, airway edema has been observed with its use in the cervical spine, prompting the FDA to issue a Public Health Notification warning for its use in cervical spine operations. To date no suitable alternative has been identified that would have similar efficacy in inducing fusion without the adverse effects of rhBMP-2 (12).

Oxysterols form a large family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some of the present inventors previously reported that specific naturally occurring oxysterols have robust osteogenic properties (13). The most potent osteogenic naturally occurring oxysterol, 20(S)-hydroxycholesterol ("20S") (14), is both osteogenic and anti-adipogenic when applied to multipotent mesenchymal cells capable of differentiating into osteoblasts and adipocytes. Structural modifications of 20S were previously performed to synthesize more potent analogues of 20S including Oxy34 and Oxy49, which were shown to induce the osteogenic and inhibit the adipogenic differentiation of bone marrow stromal cells (MSC) through activation of Hedgehog (Hh) signaling (15). Additionally, Oxy34 and Oxy49 stimulate spine fusion in vivo in a rat model of posterolateral spine fusion (15). Prior oxysterol molecules have properties that vary widely and unpredictably. There remains a need for new improved oxysterols as compared with rhBMP-2 and prior oxysterols, to provide increased potency and enhanced efficacy, and ease of synthesis and lower production cost. A new oxysterol could make a more feasible clinical option for physicians treating, for example, long bone fractures, spine disorders, and osteoporosis.

DESCRIPTION OF THE DRAWINGS

FIG. 3 shows that oxy133 induces osteogenic differentiation.

FIG. 4 shows the role of Hedgehog pathway in Oxy133-induced osteogenic differentiation.

FIG. 7 shows histological analysis of the effect of Oxy133 on spinal fusion.

DESCRIPTION

Figure 1:
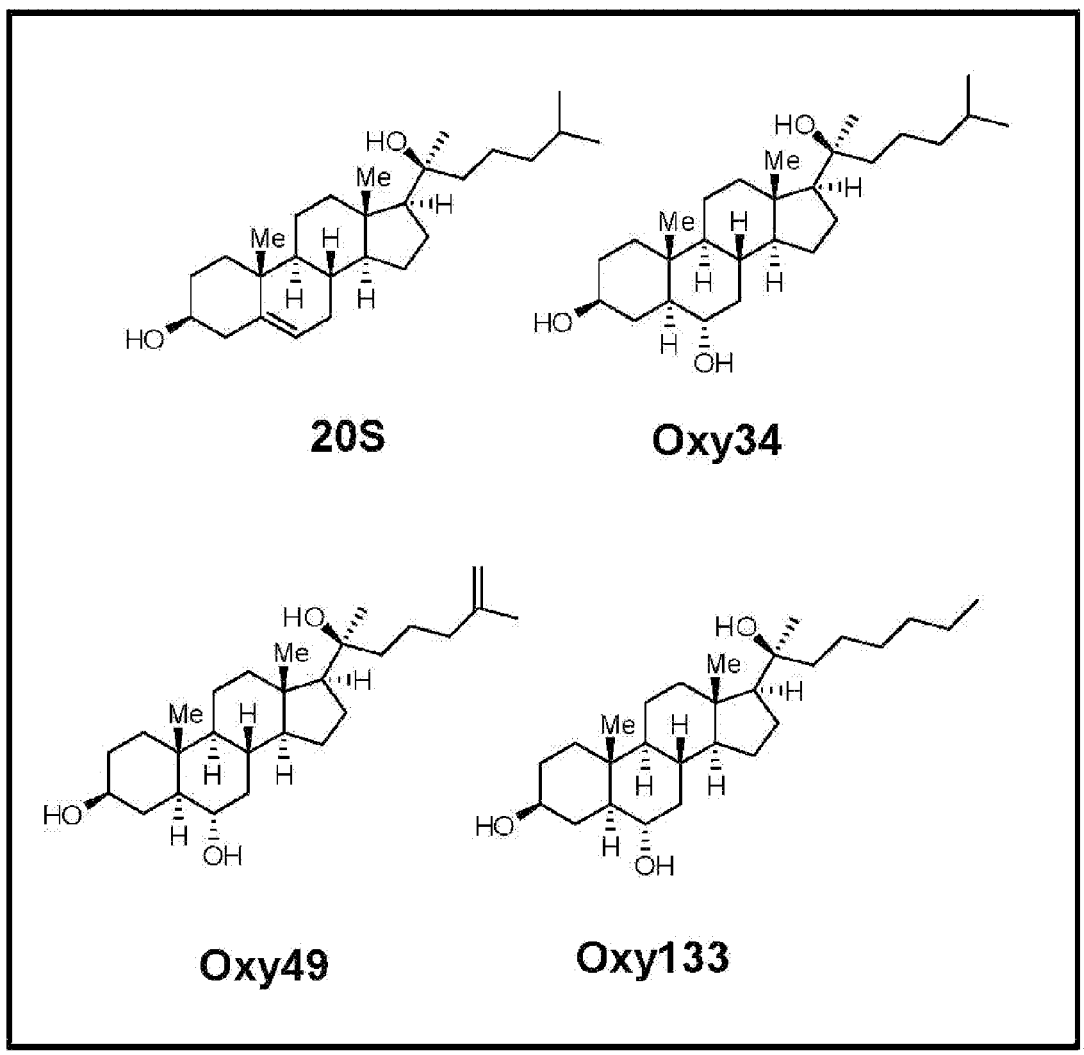
FIG. 1 shows the molecular structures of osteogenic oxysterols. The molecular structures of 20(S)-hydroxycholesterol (20S), Oxy34, Oxy49, and Oxy133 are shown. Oxy34 is different from 20S in having an extra OH group on C6 and the double bond between C5 and C6 is eliminated. Oxy49 has a similar structure to Oxy34 and includes a double bond between C25 and C27. Oxy133 differs from Oxy34 and 49 by the deletion of C27 and increasing the length of the side chain by one carbon.

The present inventors identify herein an osteogenic oxysterol, Oxy133 which is well-suited for a variety of clinical uses, and describe its ability to promote osteogenic differentiation in vitro and spine fusion in a rat model in vivo. Of the large number of oxysterol analogues synthesized and tested, Oxy133 was unexpectedly particularly effective and easy to synthesize. Oxy133 induced significant expression of osteogenic markers Runx2, osterix (OSX), alkaline phosphatase (ALP), bone sialoprotein (BSP), and osteocalcin (OCN) in C3H10T½ mouse embryonic fibroblasts. Oxy133-induced activation of an 8×-Gli luciferase reporter, its direct binding to Smoothened, and the inhibition of Oxy133-induced osteogenic effects by the Hedgehog (Hh) pathway inhibitor, cyclopamine, demonstrated a role of the Hh pathway in mediating osteogenic responses to Oxy133. In addition, Oxy133 induced the expression of OSX, BSP, and OCN and stimulated robust mineralization in primary human mesenchymal stem cells. In vivo, bilateral spine fusion in animals treated with Oxy133 at the fusion site was observed on X-ray after only 4 weeks and confirmed with manual assessment, micro-CT, and histology after 8 weeks, with equal efficiency to bone morphogenetic protein-2 (BMP2). However, unlike BMP2, Oxy133 did not induce adipogenesis in the fusion mass and resulted in the formation of denser bone as evidenced by greater BV/TV ratio and smaller trabecular separation. Oxy133 is thus useful for treating conditions that would benefit from localized stimulation of bone formation, including. e.g, spine fusion, fracture repair, bone regenerative/tissue engineering applications, augmentation of bone density in the jaw for dental implants, osteoporosis or the like.

The inventors also demonstrate that Oxy133 inhibits adipogenesis of pluripotent MSC cells. Oxy133 is thus useful for treating conditions such as, e.g., xanthoma formation, localized accumulation of fat pads and obesity.

Advantages of Oxy133 include, e.g., greater ease of synthesis and improved time to fusion when compared to other osteogenic oxysterols studied by the inventors. Oxy133 is a small molecule osteogenic oxysterol that can serve as a member of the next generation of bone anabolic therapeutic agents, as well as a useful agent for treatment of a variety of other conditions, including conditions which would benefit from a stimulation of a Hh pathway activity.

One aspect of the invention is a compound, named Oxy133, having the formula

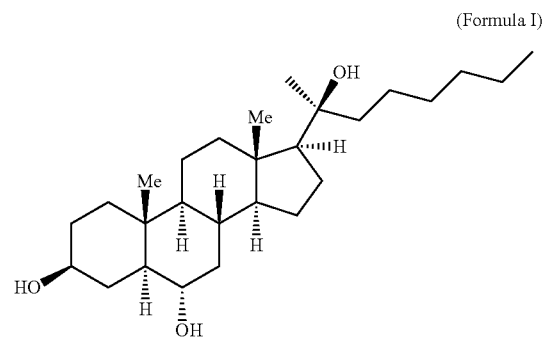

(Formula I)

or a pharmaceutically acceptable salt or solvate thereof.

Another aspect of the invention is a bioactive or pharmaceutical composition comprising Oxy133 or a pharmaceutically acceptable salt or solvate thereof and a pharmaceutically acceptable carrier. The terms "bioactive" composition or "pharmaceutical" composition are used interchangeably herein. Both terms refer to compositions that can be administered to a subject, used to coat or be present in a medical device that is introduced into a subject, or the like. These bioactive or pharmaceutical compositions are sometimes referred to herein as "pharmaceutical compositions or bioactive compositions of the invention." Sometimes the phrase "administration of Oxy133" is used herein in the context of administration of this compound to a subject (e.g., contacting the subject with the compound). It is to be understood that the compound for such a use can generally be in the form of a pharmaceutical composition or bioactive composition comprising the Oxy133.

Another aspect of the invention is a method for inducing (stimulating, enhancing) a hedgehog (Hh) pathway mediated response, in a cell or tissue, comprising contacting the cell or tissue with an effective amount (e.g. a therapeutically effective amount) of Oxy133. The cell or tissue can be in vitro or in a subject, such as a mammal (e.g. a human). In embodiments of the invention, the hedgehog (Hh) pathway mediated response is the stimulation of osteoblastic differentiation, osteomorphogenesis, and/or osteoproliferation; or it is the stimulation of hair growth and/or cartilage formation (e.g., a method for treating a subject having alopecia, or having osteoarthritis, respectively, comprising administering to the subject an effective amount of a bioactive composition of the invention); or it is the stimulation of neovasculogenesis, e.g. angiogenesis, thereby enhancing blood supply to ischemic tissues (e.g. a method for treating a subject having a cardiovascular disorder, arteriosclerosis, myocardial infarction, angina pectoris, peripheral vascular disease, and/or stroke, comprising administering to the subject an effective amount of the bioactive composition of the invention); or it is the inhibition of adipocyte differentiation, adipocyte morphogenesis, and/or adipocyte proliferation (e.g., a method for treating a subject having xanthoma formation, localized accumulation of fat pads, and/or obesity, comprising administering to the subject an effective amount of a bioactive composition of the invention); or it is the stimulation of progenitor cells to undergo neurogenesis (neuronal differentiation) (e.g., a method for treating a subject having a neurological disorder). The Hh mediated response can comprise the regeneration of any of a variety of types of tissues, for use in regenerative medicine.

Another aspect of the invention is a method for treating a subject having a bone disorder, osteopenia, osteoporosis, or a bone fracture, comprising administering to the subject an effective amount of a bioactive composition or pharmaceutical composition comprising Oxy133. The subject can be administered the bioactive composition or pharmaceutical composition at a therapeutically effective dose in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose in an effective dosage form at a selected interval to ameliorate the symptoms of osteoporosis. In one embodiment, the subject is treated to induce bone formation by harvesting mammalian mesenchymal stem cells (e.g., from the subject or from a suitable mammal, or from a tissue or cell bank), treating the mammalian mesenchymal cells with Oxy133 to induce osteoblastic differentiation of the cells, and administering the differentiated cells to the subject.

In any of the methods of the invention, the Oxy133 can be administered to a cell, tissue or organ by local administration. For example, the Oxy133 can be applied locally with a cream or the like, or it can be injected or otherwise introduced directly into a cell, tissue or organ, or it can be introduced with a suitable medical device (e.g. an implant).

Another aspect of the invention is a kit for carrying out one or more of the methods described herein. The kit can comprise an effective amount (e.g. a therapeutically effective amount) of Oxy133, optionally in a container.

Another aspect of the invention is an implant for use in the body of a subject (e.g., an animal such as a human) comprising a substrate having a surface. The surface or the inside of the implant comprises a bioactive composition or pharmaceutical composition comprising Oxy133 in an amount sufficient to induce bone formation in the surrounding bone tissue. In embodiments, the substrate is formed into the shape of a pin, screw, plate, or prosthetic joint.

Optionally, a bioactive composition, method, kit or medical device of the invention can comprise one or more other suitable therapeutic agents, such as, e.g., parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, BMP 2, BMP 4, BMP 7, and/or BMP 14.

Oxy133 has the structure

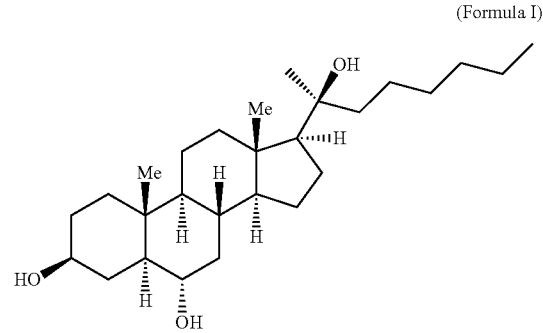

(Formula I)

Its chemical name is (3S,5S,6S,8R,9S,10R,13S,14S,17S) 17-((S)-2-hydroxyoctan-2-yl)-10,13-dimethylhexadecahydro-1H-cyclopenta[a]phenanthrene-3,6-diol.

Example II describes the design of Oxy133 and a procedure for synthesizing the molecule.

In addition to the compound Oxy133 as shown in Formula I, other embodiments of the invention encompass any and all individual stereoisomers at any of the stereocenters shown in the Formula, including diastereomers, racemates, enantiomers, and other isomers of the compound. In embodiments of the invention, "Oxy133" or a "compound having Formula I" or "Oxy133 or a pharmaceutically acceptable salt thereof" may include all polymorphs and solvates of the compound, such as hydrates and those formed with organic solvents. A "solvate" is a complex or aggregate formed by one or more molecules of a solute, e.g. a compound or a pharmaceutically-acceptable salt thereof, and one or more molecules of a solvent. Such solvates can be crystalline solids having a substantially fixed molar ratio of solute and solvent. Suitable solvents will be known by those of ordinary skill in the art, e.g., water, ethanol. Such isomers, polymorphs, and solvates may be prepared by methods known in the art, such as by regiospecific and/or enantioselective synthesis and resolution.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

It is to be understood that references herein to "Oxy133" include pharmaceutically acceptable salts or solvates thereof.

In any of the methods, compositions or kits of the invention, particularly for use in treating a subject, a composition of the invention may optionally be in combination with one or more other suitable therapeutic agents. Any therapeutic agent that is suitable for treatment of a particular condition can be used. Suitable such agents or drugs will be evident to one skilled in the art. For example, for the treatment of bone disorders, a conventional therapeutic drug can be used in combination with a composition of the invention. Some such agents include, e.g., parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, BMP 2, BMP 4, BMP 7, and/or BMP 14. For treatment of a cardiovascular or lipid disorder, a statin or a blood pressure medication can be used in combination with a composition of the invention.

A composition or compound of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier is naturally selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, dimethylsulfoxide (DMSO), ethanol, or the like.

One of skill in the art will appreciate that a particular formulation of the invention will depend, at least in part, upon the particular agent or combination of agents that is employed and the chosen route of administration. Accordingly, there is a wide variation of suitable formulations of compositions of the present invention. Some representative formulations are discussed below. Others will be evident to a skilled worker. In general, Oxy133 is administered locally or directly to a cell, tissue or organ in need of treatment. Systemic administration may also be used if desirable outcomes are achieved in the tissue or organ being treated.

Formulations or compositions suitable for oral administration can consist of liquid solutions, such as an effective amount of Oxy149 dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g., intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (i.e., lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Oxy133, alone or in combination with other therapeutic agents, can be made into aerosol formulations to be administered via inhalation. These aerosol formulations can be placed into pressurized acceptable propellants, such as dichlorodifluoromethane, propane, nitrogen, and the like.

Suitable formulations for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

Other suitable formulations include, e.g., hydrogels and polymers suitable for timed release of Oxy133, or nanoparticles for small dose delivery of Oxy133, Such formulations are well-known to those of skill in the art.

A person skilled in the art will appreciate that a suitable or appropriate formulation can be selected, adapted or developed based upon the particular application at hand. In addition, the pharmaceutical compositions of the present invention may be prepared for administration by a variety of different routes. Examples of local or direct administration include, but are not limited to, administrations performed intraarticularly, intracranially, intradermally, intrahepatically, intramuscularly, intraocularly, intraperitoneally, intrathecally, intravenously, subcutaneously, transdermally, or directly into a bone region atherosclerotic site, such as by direct injection, introduction with a catheter or other medical devise, topical application, direct application, and/or by implanting a device into in an artery or other appropriate tissue site.

Oxy133 may be formulated to be contained within, or adapted to release by a surgical or medical device or implant. In certain aspects, an implant may be coated or otherwise treated with Oxy133. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, angioplasty balloons, stents, drug-eluting stents, sutures, prosthesis, vascular catheters, dialysis catheters, vascular grafts, bone grafts, prosthetic heart valves, cardiac pacemakers, implantable cardioverter defibrillators or IV needles. Merely by way of example, a stent or stent graft typically can include a slender fabric tubular graft portion and is normally used to reinforce or strengthen a weak spot in a body passageway, such as a blood vessel. Insertion of a stent graft may be performed by use of a catheter. Placement may be facilitated by balloon expansion, such as during or following a balloon angioplasty procedure, or, alternatively, the stent graft may be self expanding.

An "effective amount" of Oxy133, as used herein, refers to an amount that can bring about at least a detectable effect. A "therapeutically effective amount," as used herein, refers to an amount that can bring about at least a detectable therapeutic response in a subject being treated (e.g., the amelioration of one or more symptoms) over a reasonable period of time.

In embodiments of the invention, Oxy133 can stimulate or inhibit a therapeutic response, as measured by any of a variety of conventional assays, by about 1%, 5%, 10%, 20%, 30%, 40%, 50% 150%, 200% or more of that in an untreated control sample. Intermediate values in these ranges are also included.

Dosages for Oxy133 can be in unit dosage form, such as a tablet or capsule. The term "unit dosage form," as used herein, refers to physically discrete units suitable as unitary dosages for animal (e.g., human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can routinely determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds, for example, Oxy133, by a direct or indirect analysis of appropriate patient samples (e.g., blood and/or tissues), in addition to analyzing the appropriate clinical symptoms of the disease, disorder, or condition.

The exact dose of Oxy133 or composition thereof administered to an animal, such as a human, in the context of the present invention will vary from subject to subject, depending on the species, age, weight and general condition of the subject, the severity or mechanism of any disorder being treated, the particular agent or vehicle used, its mode of administration, other medications the patient is taking and other factors normally considered by an attending physician, when determining an individual regimen and dose level appropriate for a particular patient, and the like. The dose used to achieve a desired concentration in vivo will be determined by the potency of the form of the Oxy133, the pharmacodynamics associated with the Oxy133 in the host, with or without additional agents, the severity of the disease state of infected individuals, as well as, in the case of systemic administration, the body weight and age of the individual. The size of the dose may also be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about 100 ng to about 600 mg, or from about 1 mg to about 500 mg, or from about 20 mg to about 400 mg, or from about 40 mg to about 200 mg of Oxy133 or a composition comprising Oxy133. In one embodiment of the invention, amounts of Oxy133 as above (e.g., a few grams) are administered locally, such as. in a spine fusion procedure as part of a scaffold.

A dose can be administered once per day, twice per day, four times per day, or more than four times per day as required to elicit a desired therapeutic effect. For example, a dose administration regimen can be selected to achieve a blood serum concentration of a compound of the present invention in the range of from about 0.01 to about 1000 nM, or from about 0.1 to about 750 nM, or from about 1 to about 500 nM, or from about 20 to about 500 nM, or from about 100 to about 500 nM, or from about 200 to about 400 nM. For example, a dose administration regime can be selected to achieve an average blood serum concentration with a half maximum dose of a compound of the present invention in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

Certain embodiments of the invention may also include treatment with an additional agent which acts independently or synergistically with the Oxy133 to improve the therapeutic results. When given in combined therapy, the agent other than Oxy133 can be given at the same time as the Oxy133, or the dosing can be staggered as desired. The two (or more)

drugs also can be combined in a composition. Doses of each can be less when used in combination than when either is used alone. Suitable doses can be determined by a skilled worker, using standard dosage parameters.

As used herein, the singular forms "a," "an" and "the" include plural referents unless the context clearly dictates otherwise.

A "subject," as used herein, includes any animal that exhibits a symptom of a condition that can be treated with Oxy133. Suitable subjects (patients) include laboratory animals (such as mouse, rat, rabbit, or guinea pig), farm animals, and domestic animals or pets (such as a cat, dog or horse). Non-human primates including human patients, are included. Typical subjects include animals that exhibit aberrant amounts (lower amounts than a "normal" or "healthy" subject) of one or more physiological activities that are stimulated by Hedgehog signaling. The aberrant activities may be regulated by any of a variety of mechanisms, including activation of a Hedgehog activity. The aberrant activities can result in a pathological condition.

One embodiment of the invention is a kit useful for any of the methods disclosed herein, either in vitro or in vivo. Such a kit comprises Oxy133 or a bioactive or pharmaceutical composition thereof, and can comprise one or more other oxysterols, e.g. which result in an increase in a Hh pathway-mediated activity, or other suitable therapeutic agents. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

A variety of conditions can be treated with Oxy133, used alone or in combination with other therapeutic agents.

As shown, e.g., in the Examples herein, Oxy133 results in an increase in hedgehog pathway activity. Without wishing to be bound by any particular mechanism, it is suggested that this increase is due to a direct binding of Oxy133 to the Smoothened receptor, an early mediator of the Hedgehog pathway from extracellular to intracellular compartments.

One effect of Oxy133 is to target pluripotent cells to induce their lineage specific differentiation into various cell types, e.g., osteoblasts, For example, as shown in the Examples, mesenchymal stem cells treated with Oxy133 showed induced expression of markers of osteoblast differentiation. Without wishing to be bound by any particular mechanism, it is suggested that this lineage specific differentiation is due to the induction of Hedgehog signaling in these cells. However, methods of treatment discussed herein are included in the present invention, regardless of the mechanism by which the Oxy133 functions. Oxy133 is useful for treating conditions which would benefit from stimulation of bone formation, osteoblastic differentiation, osteomorphogenesis and/or osteoproliferation. Among these conditions or treatments are, e.g., osteoinductive therapy for stimulation of localized bone formation in spine fusion or osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders in which native bone growth is inadequate, which will be evident to skilled workers. Treatment can be administered to treat open fractures and fractures at high risk of non-union, and in subjects with spinal disorders, including subjects in need of spine fusion (e.g., anterior lumbar interbody fusion, posterior lumbar spinal fusion, and cervical spine fusion) or subjects having degenerative disc disease or arthritis affecting the lumbar and cervical spine. Furthermore, Oxy133 can be used to treat osteoporosis, particularly in the aging population, resulting from increased bone resorption by osteoclasts in parallel with decreased bone formation by osteoblasts.

More particularly, the following types of bone-related treatments can be carried out:

1. Oxy133 is used as an osteogenic agent delivered locally in the body in order to stimulate localized bone formation, using a scaffold that is composed of a compatible molecule such as but not limited to collagen I, which absorbs Oxy133 and then is placed inside the body. For example the scaffold containing Oxy133 and which can be placed in between transverse processes or in the intervertebral disc where the fusion of two or more vertebrae is indicated, for example in spine fusion, pseudoarthrosis, and non-union fusions. In other embodiments, the scaffold containing Oxy133 is placed in a fractured bone in order to simulate bone formation and healing of the fracture; is placed in a bone defect such as calvarial or maxillofacial bone defects where bone regeneration by Oxy133 is indicated; or is placed in the jaw bone in order to stimulate bone formation as a means of regenerating bone prior to dental procedures such as dental implants.

2. Oxy133 is used as an osteogenic agent in vitro For example, it is administered to osteoprogenitor cells, for example mesenchymal stem cells, in order to stimulate their osteogenic differentiation prior to the application of such cells in orthopedic and other procedures as indicated in 1) above order to stimulate localized bone formation.

3. Oxy133 is used in vitro in order to stimulate the Hedgehog signaling pathway in osteoprogenitor cells, thereby leading to the osteogenic differentiation of the cells in vitro or in vivo.

Another effect of Oxy133 is to inhibit adipocyte differentiation, adipocyte morphogenesis, and/or adipocyte proliferation. Among the conditions which can be treated by virtue of this effect of Oxy133 are, e.g. xanthoma formation, localized accumulation of fat pads and obesity.

Other conditions that would directly or indirectly benefit from local administration of Oxy133 include the need for hair growth, neurogenesis, cartilage formation etc. or cardiovascular disorders, which conditions are related to stimulation of Hedgehog pathway activity by acting on cells, tissues or organs relevant to each indication.

In the foregoing and in the following examples, all temperatures are set forth in uncorrected degrees Celsius; and, unless otherwise indicated, all parts and percentages are by weight.

EXAMPLES

Example I

Materials and Methods

Cell Culture and Reagents

Mouse multipotent bone marrow stromal cell (MSC) line, M2-10B4 (M2), and embryonic fibroblast cell line C3H10T½ (C3H) were purchased from American Type Culture Collection (Rockville, Md.) and cultured as we have previously reported (14, 15). Treatment to induce osteogenic differentiation was performed in RPMI for M2 cells or DMEM for C3H cells containing 5% fetal bovine serum, 50 μg/ml ascorbate, and 3 mM β-glycerophosphate (βGP) (differentiation media). Cyclopamine was purchased from EMD Biosciences, Inc. (La Jolla, Calif.). Primary human mesenchymal stem cells (HMSC) were purchased from Lonza (Walkersville, Md.), cultured and passaged in growth medium from StemCell Technologies (Vancouver, Canada) according to manufacturer's instructions. Osteogenic differentiation of HMSC was induced by treating the cells in DMEM low glucose containing antibiotics and 10% heat-inactivated FBS, 10-8 M dexamethasone, 10 mM βGP, and 0.2 mM ascorbate.

Alkaline Phosphatase Activity and Von Kossa Staining

Alkaline phosphatase (ALP) activity assay on whole cell extracts (13, 14), and von Kossa staining of cell monolayers for mineralization (16) were performed as previously described.

Quantitative RT-PCR

Total RNA was extracted with the RNA isolation Trizol reagent from Ambion, Inc. (Austin, Tex.) according to the manufacturer's instructions. RNA (1 μg) was reverse-transcribed using reverse transcriptase from Bio-Rad (Hercules, Calif.) to make single stranded cDNA. Q-RT-PCR reactions were performed using iQ SYBR Green Supermix and an iCycler RT-PCR Detection System (Bio-Rad). Primer sequences for mouse genes Gli-1, Patched1 (Ptch1), bone-liver-kidney isozyme of alkaline phosphatase (ALP), bone sialoprotein (BSP), Runx2, osterix (OSX), osteocalcin (OCN) and GAPDH were used as previously described (14). Human primers sequences were: GAPDH 5'-CCT CAA GAT CAT CAG CAA TGC CTC CT (SEQ ID NO:1) and 3'-GGT CAT GAG TCC TTC CAC GAT ACC AA (SEQ ID NO:2), BSP 5'-AGA AGA GGA GGA GGA AGA AGA GG (SEQ ID NO:3) and 3'-CAG TGT TGT AGC AGA AAG TGT GG (SEQ ID NO:4), OSX 5'-GCG GCA AGA GGT TCA CTC GTT CG (SEQ ID NO:5) and 3'-CAG GTC TGC GAA ACT TCT TAG AT (SEQ ID NO:6); relative expression levels were calculated using the 2ΔΔCT method as previously described (15).

Transient Transfection and Gli-Dependent Reporter Assay

Cells at 70% confluence in 24-well plates were transiently transfected with Gli-dependent firefly luciferase and Renilla luciferase vectors as we have previously described (17, 18). FuGENE 6 transfection reagent (Roche Applied Science, Indianapolis, Ind.) was used at a ratio of 3:1 with nuclease-free water and total DNA per well did not exceed 500 ng. Luciferase activity was assessed using the Dual Luciferase Reporter Assay System (Promega Corporation, Madison, Wis.) according to manufacturer's instructions after cells were treated for 48 hours.

Synthesis and Molecular Characterization of Oxy133

Materials were obtained from commercial suppliers and were used without further purification. Air or moisture sensitive reactions were conducted under argon atmosphere using oven-dried glassware and standard syringe/septa techniques. The reactions were monitored on silica gel TLC plates under UV light (254 nm) followed by visualization with Hanessian's staining solution. Column chromatography was performed on silica gel 60. 1H NMR spectra were measured in CDCl3. Data obtained are reported as follows in ppm from an internal standard (TMS, 0.0 ppm): chemical shift (multiplicity, integration, coupling constant in Hz.). Stepwise detailed description of the synthesis protocol and characterization of the intermediates and final products are provided in Supplemental Material.

Smoothened Binding Assay

Interaction of oxysterol with Smoothened (Smo) was examined as we previously reported (19). Smo−/−:YFP-Smo cells (20) were lysed in hypotonic SEAT buffer (250 mM sucrose, 1 mM EDTA, 10 mM acetic acid, 10 mM triethanolamine, 10 mg/mL leupeptin-pepstatin-chymostatin (LPC) protease inhibitor mix and the SigmaFast EDTA-Free protease cocktail). After removal of nuclei by centrifugation (500×g, 5 min), membranes were pelleted by centrifugation at 95,000×g for 30 min. Membranes were extracted in an n-dodecyl-b-D-maltopyranoside (DDM) extraction buffer (50 mM Tris pH 7.4, 500 mM NaCl, 10% v/v glycerol, 0.1% w/v DDM and the SigmaFast EDTA-Free protease cocktail) for 4 hours at 4° C., followed by removal of insoluble material by centrifugation (100,000×g, 30 min). This membrane extract was incubated with 50 uM free 20(S) or Oxy133 or Oxy16 (an oxysterol analogue that does not activate Hh signaling; Parhami et al. unpublished observations) for one hour at 4° C. prior to the addition of magnetic beads coupled to nat-20(S)-yne or control magnetic beads (19). Binding reactions were incubated overnight at 4° C. In all experiments, the amount of solvent was carefully equalized in each sample. After extensive washing, proteins captured on the beads were eluted with reducing SDS sample buffer. The presence of YFP-Smo in these eluates was determined by quantitative immunoblotting with an anti-GFP antibody (Novus, NB600-308, 1:5000) and infrared imaging (Li-Cor Odyssey system).

Animals

Thirty-eight 8-week-old male Lewis rats were purchased from Charles River Laboratories (Wilmington, Mass.) and were maintained and housed at the UCLA vivarium in accordance with regulations set forth by the UCLA Office of Protection of Research Subjects. The study was performed under a protocol approved by the UCLA Animal Research Committee (ARC). All animals were euthanized using a standard CO2 chamber 8 weeks after the spinal fusion procedure, and their spines were excised and stored in 40% ethyl alcohol.

Surgical Procedures

Animals were pre-medicated with sustained release buprenorphine thirty minutes prior to surgery and anesthetized with 2% isoflurane administered in oxygen (1 L/min). The surgical site was shaved and disinfected with Betadine and 70% ethanol. Posterolateral intertransverse process spinal fusion at L4-L5 was performed as in prior studies (21, 22). The L6 vertebral body was identified using the iliac crest as a landmark. A 4-cm longitudinal midline incision was made through the skin and subcutaneous tissue over L4-L5 down to the lumbodorsal fascia. A 2-cm longitudinal paramedial incision was then made in the paraspinal muscles bilaterally to expose the transverse processes of L4-L5, which were decorticated with a high-speed burr. The surgical site was then irrigated with sterile saline, and 5 mm×5 mm×13 mm pieces of collagen sponge (Helistat, Integra Life Sciences) containing dimethyl sulfoxide (DMSO) control, rhBMP-2, or Oxy133 were placed bilaterally, with each implant spanning the transverse processes. The implants were then covered with the overlying paraspinal muscles and the lumbodorsal fascia and skin were closed with 4-0 Prolene sutures (Ethicon, Inc., Somerville, N.J.). Animals were allowed to ambulate, eat, and drink ad libitum immediately after surgery.

Radiographic Analysis

Posteroanterior radiographs of the lumbar spine were taken on each animal at 4, 6, and 8 weeks after surgery using a Faxitron LX60 cabinet radiography system and evaluated blindly by two independent observers employing the following standardized scale: 0, no fusion; 1, unilateral fusion; and 2, complete bilateral fusion. The scores from the observers were added together and only a score of 4 was considered as complete fusion.

Manual Assessment of Fusion

Eight weeks after surgery, animals were euthanized and the spines were surgically removed and evaluated by two blinded independent observers for motion between levels. Nonunion was recorded if motion was observed between the facets or transverse processes on either side. Complete fusion was recorded if no motion was observed bilaterally. Spines were scored as either fused or not fused. Unanimous agreement was required to consider complete fusion.

Micro-Computed Tomography

Each removed spine was analyzed by high resolution micro-computed tomography (micro-CT), using a SkyScan 1172 scanner (SkyScan, Belgium) with a voxel isotropic resolution of 20 μm and an X-ray energy of 55 kVp and 181 mA to further assess the fusion rate and observe the fusion mass as we have previously reported (15). Three hundred and sixty projections were acquired over an angular range of 180° with steps of 0.5 with an exposure time of 220 msec/slice. Five frames were averaged at each rotation step to get better signal to noise ratio. A 0.5 mm aluminum filter was used to narrow down the X-ray beam frequency in order to minimize beam hardening artifact. Virtual image slices were reconstructed using the cone-beam reconstruction software version 2.6 based on the Feldkamp algorithm (SkyScan). These settings produced serial cross-sectional 1024×1024 pixel images. Sample re-orientation and 2D visualization were performed using DataViewer (SkyScan). 3D visualization was performed using Dolphin Imaging version 11 (Dolphin Imaging & Management Solutions, Chatsworth, Calif.). Fusion was defined as the bilateral presence of bridging bone between the L4 and L5 transverse processes. The reconstructed images were judged to be fused or not fused by two experienced independent observers. To quantify the density of bone formed within each fusion mass, the tissue volume of the mass (TV), trabecular bone volume within the mass (BV), BV/TV ratio, trabecular thickness, and trabecular separation were calculated. This was performed using DataViewer software with measurements across 501 axial slices (20 um per slice, 10.02 mm length) within each fusion mass, centered at the level of the intervertebral body of L4-5.

Histology

After undergoing micro-CT, two representative specimens from each surgical group were processed undecalcified by dehydration, clearing in xylene and embedding in methyl methacrylate as we have previously reported (15, 23). Serial coronal sections were cut with a thickness of 5 um and stained with toluidine blue pH 6.4. Photomicrographs of sections were obtained as previously reported using a ScanScope XT System (Aperio Technologies, Inc., Vista, Calif.) at a magnification of 10× in FIG. 7A and 20× in FIG. 7B (24).

Statistical Analysis

Statistical analyses were performed using the StatView 5 program. All p values were calculated using ANOVA and Fisher's projected least significant difference (PLSD) significance test. A value of $p<0.05$ was considered significant.

Example II

Synthesis and Chemical Characterization of Oxy133

The following is the chemical structure of Oxy133:

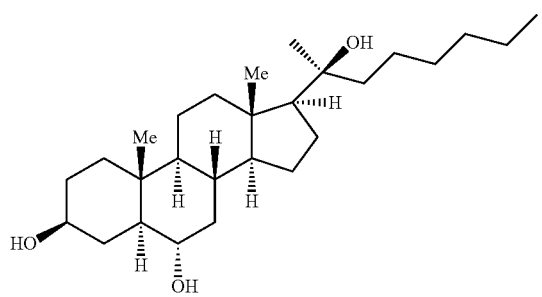

Materials were obtained from commercial suppliers and were used without further purification. Air or moisture sensitive reactions were conducted under argon atmosphere using oven-dried glassware and standard syringe/septa techniques. The reactions were monitored on silica gel TLC plates under UV light (254 nm) followed by visualization with Hanessian's staining solution. Column chromatography was performed on silica gel 60. $^1$H NMR spectra were measured in $CDCl_3$. Data obtained are reported as follows in ppm from an internal standard (TMS, 0.0 ppm): chemical shift (multiplicity, integration, coupling constant in Hz.). The following is a stepwise description of the protocol. Structures of Oxy34 and Oxy49, the synthesis of which we had previously reported [Johnson et al. (2011), *Journal of Cellular Biochemistry* 112, 1673-1684], are shown for comparison to the structure of Oxy133.

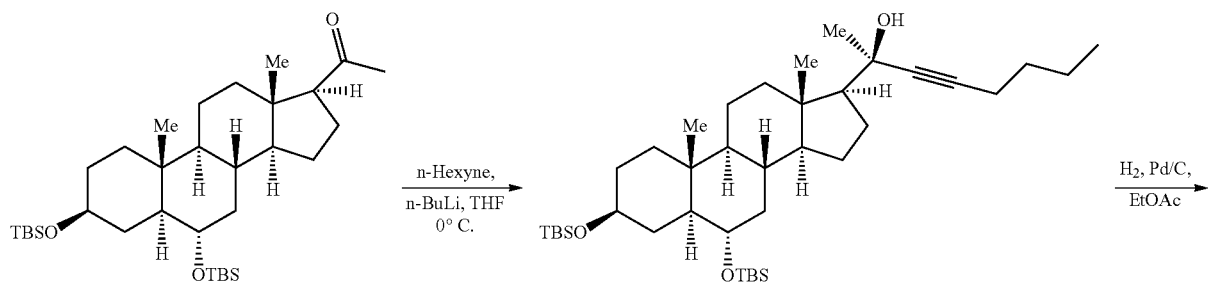

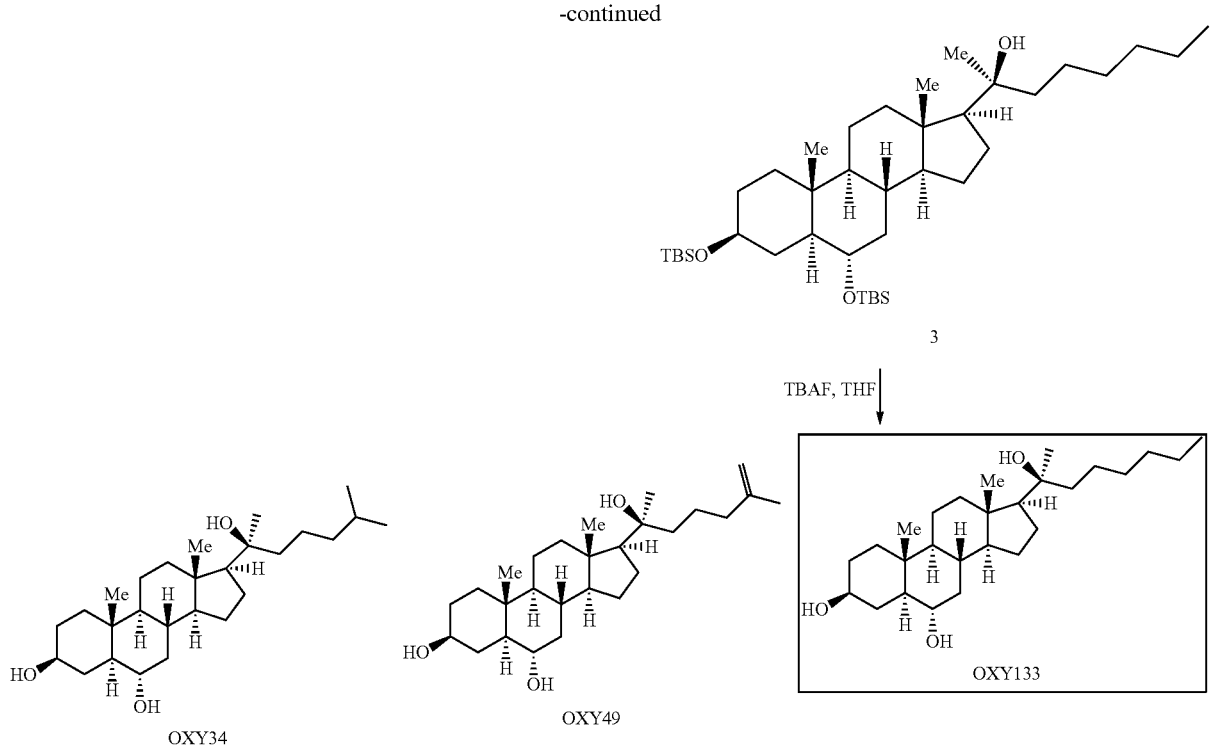

1-((3S,5S,6S,8R,9S,10R,13S,14S,17S) 3,6-Bis((tert-butyldimethylsilyl)oxy)-10,13-dimethylhexadecahydro-1H-cyclopenta[a]phenanthren-17-yl)ethanone (1)

Prepared according to a published patent procedure (Parhami et al., WO 2009/07386, p. 52) $^1$H NMR (CDCl$_3$, 400 MHz) δ: 3.47 (1H, dddd, J=11.0, 11.0, 4.8, 4.8 Hz), 3.36 (1H, ddd, J=10.4, 10.4, 4.4 Hz), 2.53 (1H, d, J=8.8, 8.8 Hz), 2.20-2.14 (1H, m), 2.10 (3H, s), 2.01-1.97 (1H, m), 1.88-1.82 (1H, m), 1.73-0.89 (17H, m), 0.88 (18H, s), 0.79 (3H, s), 0.59 (3H, s), 0.043 (3H, s), 0.04 (3H, s), 0.03 (3H, s), 0.02 (3H, s). $^{13}$C NMR (CDCl$_3$, 100 MHz) δ: 209.5, 72.2, 70.1, 63.7, 56.4, 53.7, 51.8, 44.2, 41.9, 38.9, 37.6, 36.3, 34.3, 33.2, 31.7, 31.5, 25.94, 25.92, 24.4, 22.7, 21.1, 18.3, 18.1, 13.5, 13.4, −4.1, −4.6, −4.7.

(R)-2-((3S,5S,6S,8R,9S,10R,13S,14S,17S) 3,6-Bis((tert-butyldimethylsilyl)oxy)-10,13-dimethylhexadecahydro-1H-cyclopenta[a]phenanthren-17-yl)oct-3-yn-2-ol (2)

To a cooled (0° C.) solution of n-hexyne (1.5 mL, 12 mmol) in THF (6 mL) was added a 1.6 M solution of n-butyllithium in hexanes (3.75 mL). The resulting solution was stirred for 30 min until a solution of compound 1 (1.27 g, 2.2 mmol) in THF (10 mL) was added via cannula. The mixture was warmed to room temperature over 3 h and diluted with water (40 mL) and the crude product was isolated by ethyl acetate extraction (3×30 mL). The combined organic layers were washed with brine and dried over Na$_2$SO$_4$. Concentration gave an oily product, which was purified on silica gel (hexane, ethyl acetate, gradient) to afford 1.30 g of compound 2 (92%). $^1$H NMR (CDCl$_3$, 300 MHz) δ: 3.50 (1H, ddd, J=15.9, 11.0, 4.8 Hz), 3.36 (1H, ddd, J=10.6, 10.6, 4.3 Hz), 2.18 (1H, t, J=6.9 Hz), 2.10 (1H, m), 1.91-1.62 (4H, m), 1.53-1.31 (2H, m), 1.44 (3H, s), 1.31-0.93 (22H, m), 0.93 (3H, s), 0.92 (3H, m), 0.90 (18H, s), 0.88 (3H, s), 0.61 (1H, m), 0.04 (6H, s), 0.03 (6H, s). $^{13}$C NMR (CDCl$_3$, 75 MHz) δ: 85.9, 83.9, 72.4, 71.4, 70.3, 60.5, 55.8, 53.8, 51.8, 43.5, 36.3, 33.7, 33.0, 30.7, 25.9, 22.0, 18.4, 18.3, 18.1, 13.6, 13.5, −4.7, −4.7.

(S)-2-((3S,5S,6S,8R,9S,10R,13S,14S,17S) 3,6-Bis((tert-butyldimethylsilyl)oxy)-10,13-dimethylhexadecahydro-1H-cyclopenta[a]phenanthren-17-yl)octan-2-ol (3)

Compound 2 (1.3 g, 2.0 mmol) was dissolved in ethyl acetate (5 mL) and methanol (5 mL) and Pd/C (10%, 0.1 g) was added to the solution. The mixture was degassed repeatedly under vacuum and then exposed to hydrogen gas under atmospheric pressure (balloon). After 18 h at room temperature, the mixture was diluted with ethyl acetate (20 mL) and filtered over Celite to remove the catalyst. The filter washed with ethyl acetate and the combined filtrates evaporated to afford 1.3 g of the reduced product 3, which was used without further purification. $^1$H NMR (CDCl$_3$, 300 MHz) δ: 3.50 (1H, ddd, J=15.9, 11.0, 4.8 Hz), 3.36 (1H, ddd, J=10.6, 10.6, 4.3 Hz), 2.1-1.95 (2H, m), 1.75-1.35 (10H, m), 1.32-1.29 (10H, m), 1.24 (3H, s), 0.91-1.21 (10H, m), 0.89 (18H, s), 0.82 (3H, s), 0.79 (3H, s), 0.63 (1H, m), 0.04 (6H, s), 0.03 (6H, s) $^{13}$C NMR (CDCl$_3$, 75 MHz) δ: 75.2, 72.3, 57.6, 56.4, 53.8, 51.8, 42.9, 37.6, 36.3, 33.7, 31.9, 30.0, 25.9, 22.6, 18.3, 18.1, 14.1, 13.8, 13.5, −4.6, −4.7.

(3S,5S,6S,8R,9S,10R,13S,14S,17S) 17-((S)-2-hydroxyoctan-2-yl)-10,13-dimethylhexadecahydro-1H-cyclopenta[a]phenanthrene-3,6-diol (Oxy133)

A 1 M solution of TBAF in THF (8 mL, 8 mmol, 4 equiv) was directly added to compound 3 (1.3 g, 2.0 mmol, 1.0 equiv) and the resulting solution was diluted with THF (1 mL) and stirred at room temperature for 72 h. The mixture was then diluted with water (50 mL) and extracted repeatedly with ethyl acetate (4×40 mL). The combined organic layers were washed with brine, dried over $Na_2SO_4$ and the solvent evaporated. Purification of the crude product by silica gel chromatography (hexane, ethyl acetate, gradient, then 10% methanol in ethyl acetate) afforded a white solid (0.6 g, 70%), which was subjected to trituration in aqueous acetone (acetone, water, 3:1) to obtain 0.5 g of pure Oxy133. $^1$H NMR ($CDCl_3$, 300 MHz) δ: 3.50 (1H, ddd, J=15.9, 11.0, 4.8 Hz), 3.36 (1H, ddd, J=10.6, 10.6, 4.3 Hz), 2.19 (1H, m), 2.10-1.90 (3H, m), 1.85-1.60 (7H, m), 1.55-1.38 (7H, m), 1.25 (11H, m), 1.20-0.95 (4H, m), 0.90 (3H, m), 0.86 (3H, s), 0.80 (3H, s), 0.62 (1H, m). $^{13}$C NMR ($CDCl_3$, 75 MHz) δ: 75.1, 71.1, 69.3, 57.5, 56.2, 53.6, 51.6, 44.0, 42.8, 41.4, 40.1, 37.2, 36.2, 33.5, 32.1, 31.8, 30.9, 29.9, 26.3, 24.2, 23.6, 22.5, 22.2, 20.9, 14.0, 13.6, 13.3. MS: M+H=420.36. HRMS (ESI) m/z [M-2$H_2$O H]$^+$ calcd for $C_{27}H_{44}OH$: 385.3470. found 385.3478.

Example III

Experimental Results: Stimulation of Osteogenesis of Bone Formation and Spinal Fusion In Vivo Oxy133 Induces Osteogenic Differentiation of Bone Marrow Stromal Cells, Embryonic Fibroblasts, and Human Mesenchymal Stem Cells To achieve the goal of developing a molecule capable of inducing osteogenic differentiation of osteoprogenitor cells, we modified the molecular structure of the most potent osteogenic naturally occurring oxysterol, 20(S)-hydroxycholesterol (20S) based on our understanding of the structure activity relationships observed in over 100 previously synthesized analogues. We previously reported that robust osteogenic differentiation was achieved with two structural analogues of 20S, Oxy34 and Oxy49 (15). These molecules were formed by adding an a hydroxyl (OH) group on carbon 6 (C6) in both Oxy34 and 49, and a double bond between C25 and C27 in Oxy49 (FIG. 1) (15). In studies reported here, we attempted to further improve on these two molecules by developing a more easily synthesized and more potent analogue that would be suitable for scale up into large amounts for future preclinical and clinical studies in large animals and humans, respectively. This molecule could be a candidate for therapeutic development and clinical use to increase bone formation locally for stimulation of spinal fusion and fracture healing, and perhaps even systemically to address disorders such as osteopenia and osteoporosis. Through structure activity relationship studies a novel analogue, Oxy133, was synthesized according to the protocol described in Example II and tested for osteoinductive activity. Oxy133 differs from Oxy34 and 49 by the deletion of C27 and increasing the length of the side chain by one carbon (FIG. 1). Importantly, Oxy133 can be more readily prepared on large scale due to inexpensive commercially available starting materials that result in a significantly less costly product compared to Oxy34 and Oxy49. Moreover, the alkyne addition used in the preparation of Oxy133 is superior to the Grignard chemistry used in the synthesis of Oxy34 and Oxy49 in terms of yield, purity of products (diastereoselectivity), and scalability.

Figure 2A:
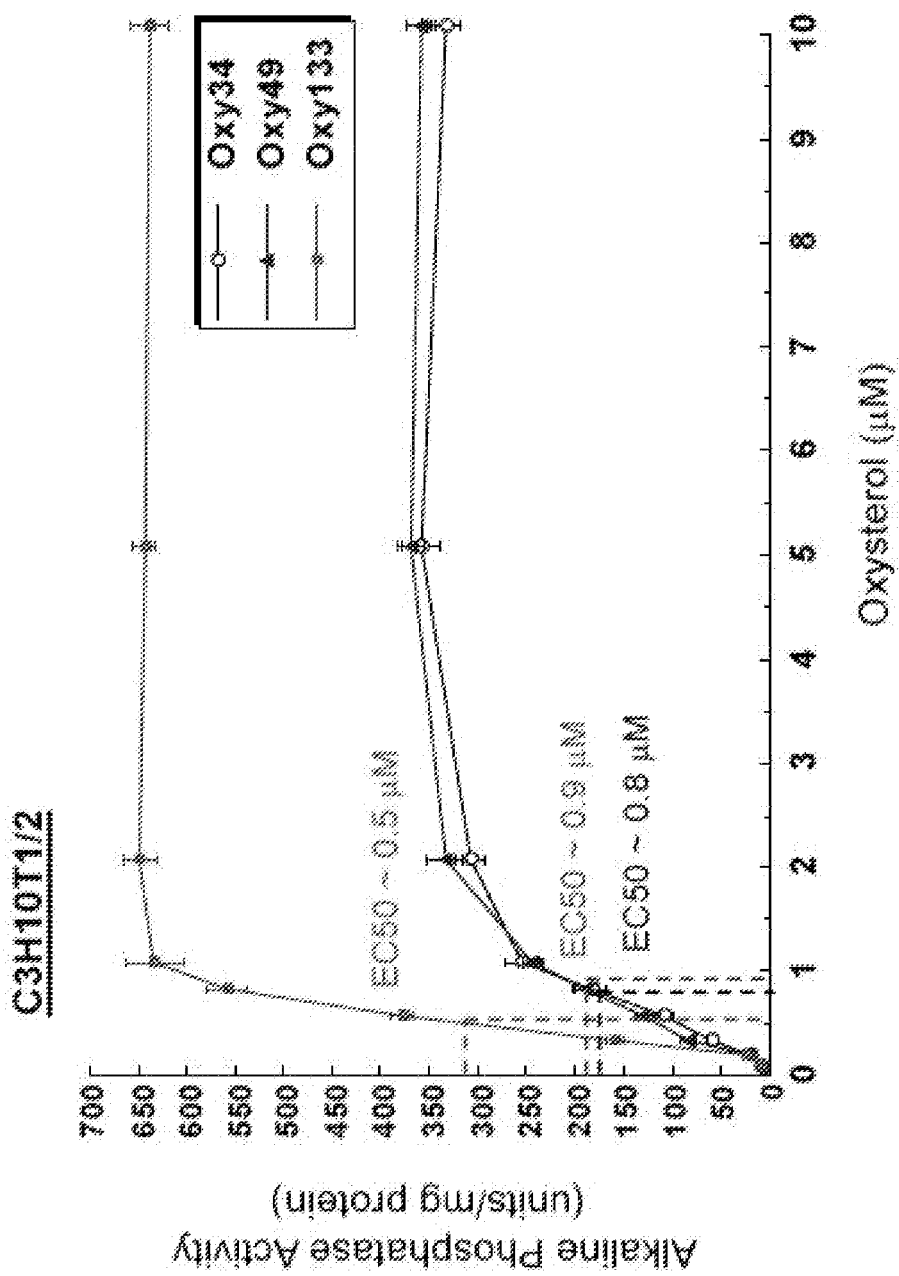
(FIG. 2A) C3HT101/2 cells or (FIG. 2B) M2-10B4 cells at confluence were treated with control vehicle or 0.125-10 µM of Oxy133. For direct comparison to Oxy133, C3H cells were also treated with Oxy34 and Oxy49 (FIG. 2A). After 4 days, alkaline phosphatase (ALP) activity was measured in whole cell extracts. Data from a representative of three separate experiments are reported as the mean of triplicate determinations+SD and normalized to protein concentration. ($p<0.0001$ for cells treated with 0.25 µM or higher dose of all oxysterols vs. control vehicle treated cells).
Figure 2B:
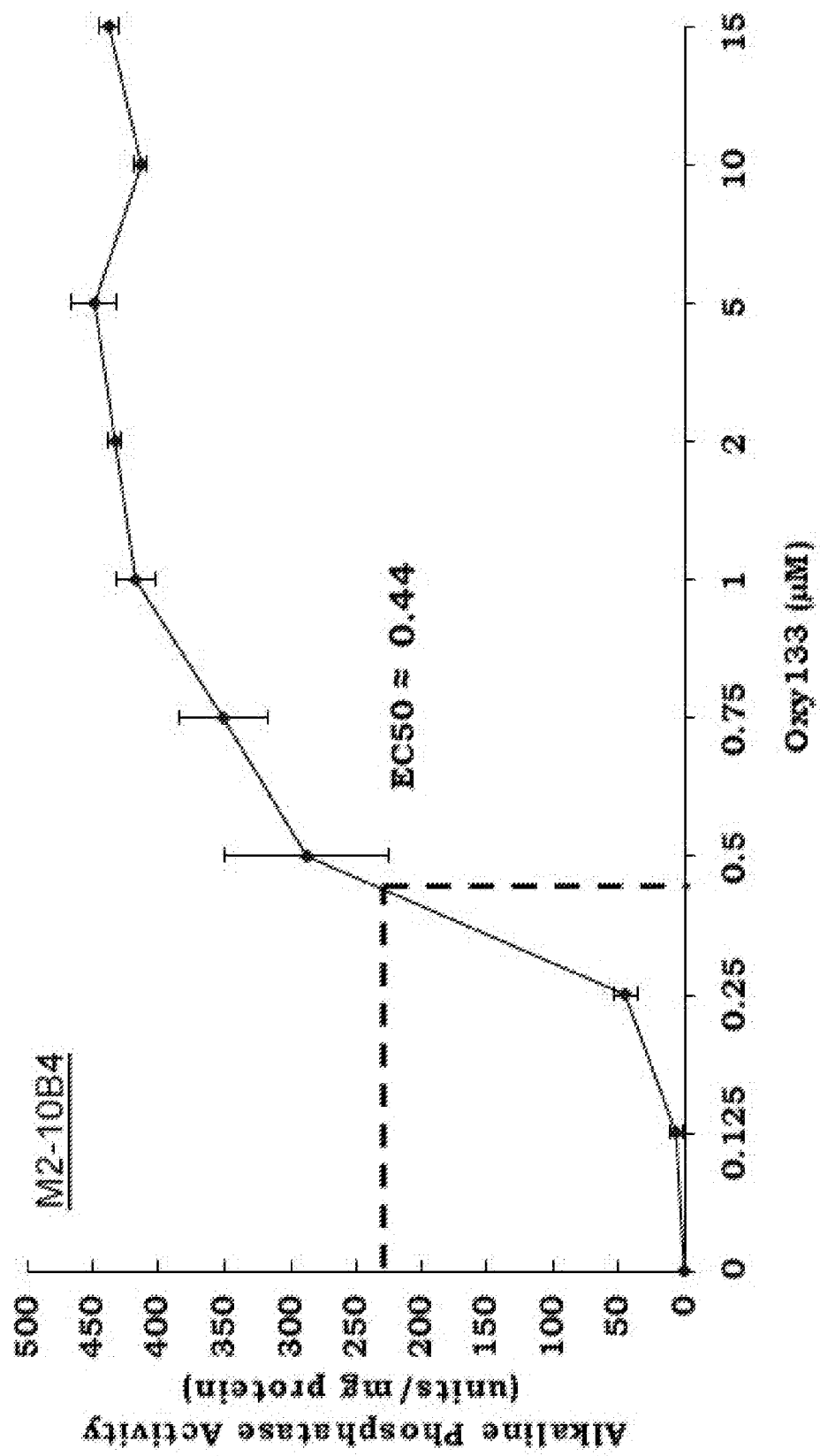
FIG. 2 shows the dose-dependent activation of alkaline phosphatase activity by oxysterols.
Figure 3A:
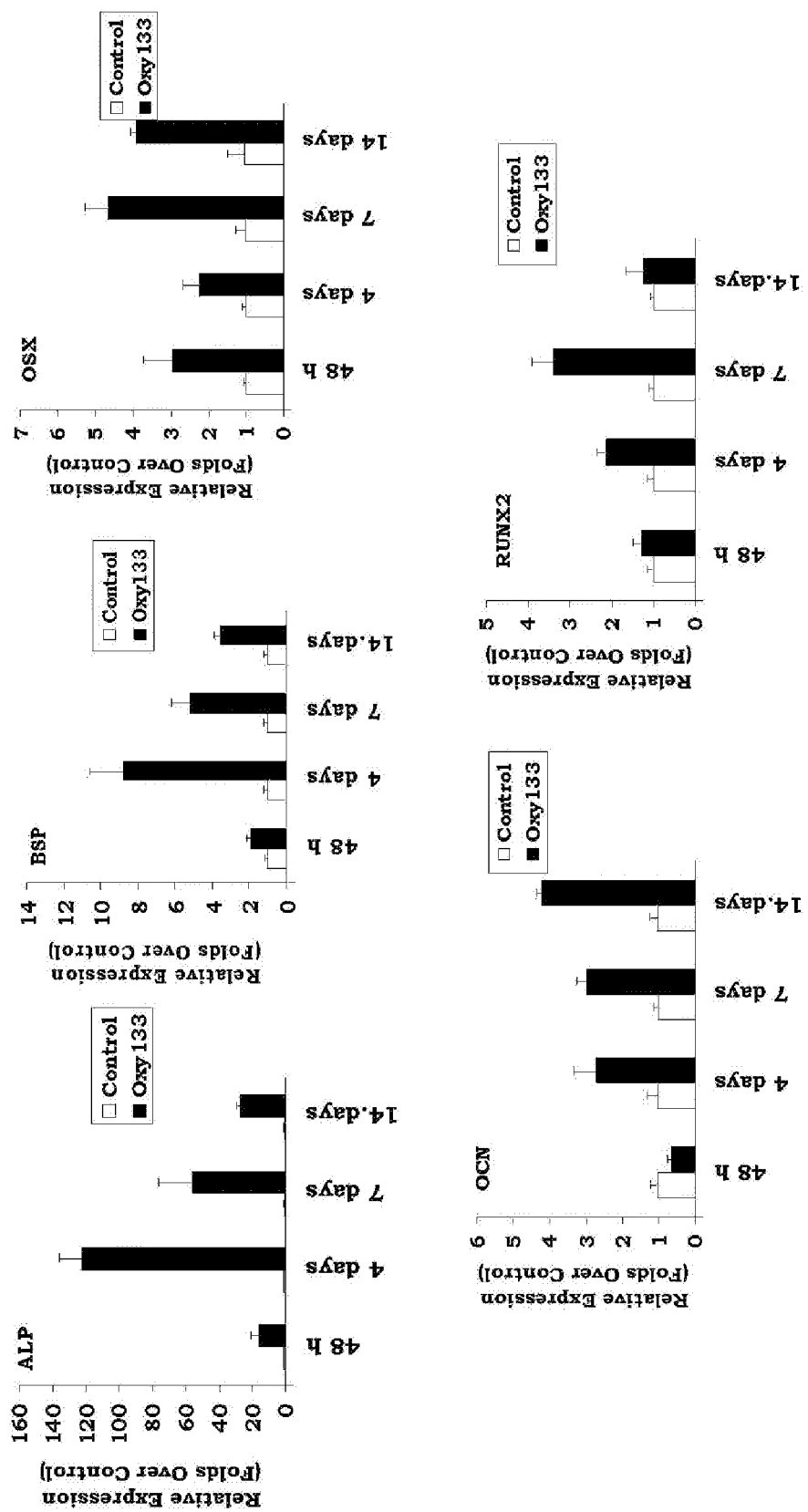
(FIG. 3A) C3HT101/2 cells at confluence were treated with control vehicle or 2.5 µM Oxy133 in osteogenic media. Expression of osteogenic genes Runx2, ALP, BSP, OSX, and OCN was measured by quantitative real-time PCR after 48 hours (48 h), 4, 7, and 14 days of treatment. Results from a representative experiment are reported as the mean of triplicate determinations±SD. ($p<0.005$ for control vs. Oxy133 at all time points for ALP, BSP and OSX and at 4, 7, and 14 days for Runx2 and OCN).
Figure 3B:
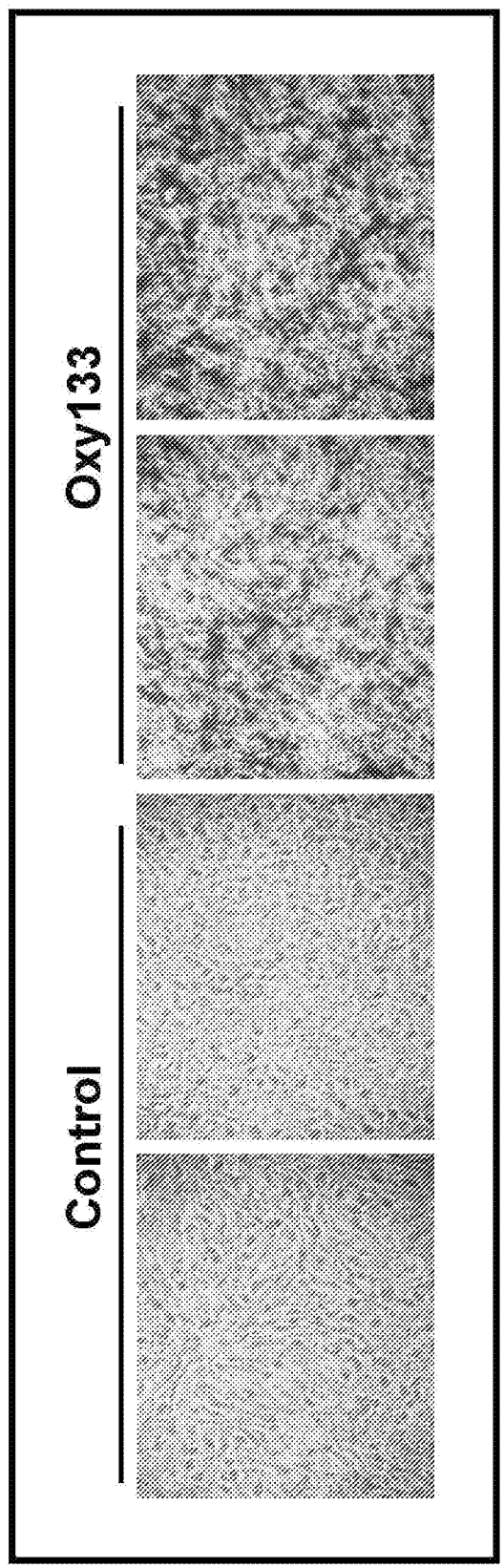
(FIG. 3B) C3H10T½ cells were treated with control vehicle or 2.5 µM Oxy133 for 3 weeks. To examine extracellular mineralization von Kossa staining was performed and mineralized matrix appears as dark black staining under light microscopy (10×).
Figure 3C:
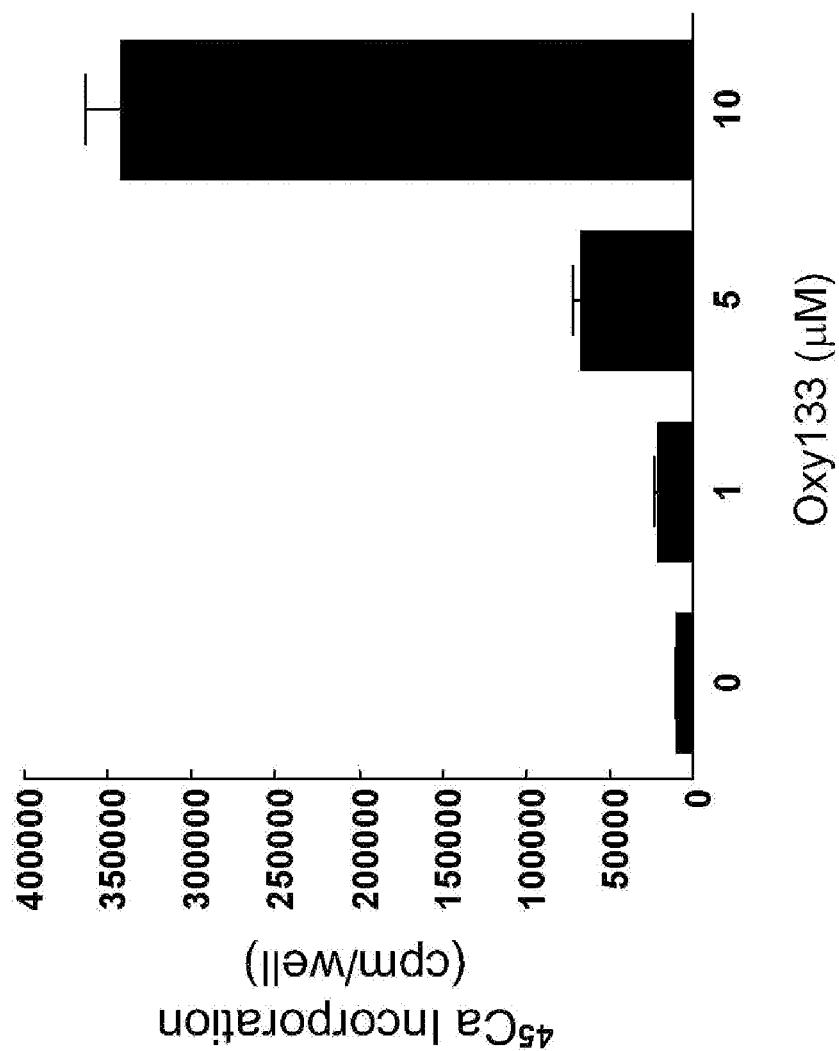
(FIG. 3C) In parallel cultures to those described in (B), mineralization was quantified using a 45 Ca incorporation assay ($p<0.005$ for control vs. all concentrations of Oxy133).

As compared with other structural analogues of 20S, Oxy133 has surprisingly improved potency in inducing alkaline phosphatase (ALP) activity as measured by ALP enzymatic activity assay in C3H and M2 cells. This is a useful model for osteogenic activity, as we have previously reported for other oxysterol analogues (15). A dose-dependent increase in ALP activity was observed with Oxy133 at low micromolar (µM) concentrations (FIG. 2A, B). The EC50 for Oxy133 was found to be approximately 0.5 µM in C3H (FIG. 2A) and 0.44 µM in M2 cells (FIG. 2B). The EC50 of Oxy34 and Oxy49 in C3H cells was found to be similar to what was previously reported in M2 cells, 0.8 and 0.9 µM, respectively, and significantly higher than the EC50 of Oxy133 (FIG. 2A). Moreover, Oxy133 at high doses induced a greater level of ALP activity than similar doses of Oxy34 and Oxy49 in C3H cells (FIG. 2A). Oxy133 was found to have other beneficial effects in inducing osteogenic differentiation of cells through analysis of the expression of osteogenic differentiation marker genes Runx2, Osterix (OSX), ALP, bone sialoprotein (BSP), and osteocalcin (OCN). In C3H cells treatment with 2.5 µM Oxy133 induced Runx2 expression 2 and 3.2 fold after 4 and 7 days of treatment, respectively, which returned to baseline levels at 14 days (FIG. 3A). OSX expression was significantly induced 3 fold after 2 days and remained elevated throughout the experiment reaching a maximum induction of 4.5 fold (FIG. 3A). Treatment of C3H cells with Oxy133 induced the expression of ALP 18 fold after 2 days which maximized to 120 fold after 4 days and then dropped to 22 fold after 7 and 14 days, respectively (FIG. 3A). BSP expression was maximally induced 9 fold on day 4 and remained induced for the duration of the experiment in spite of lowering with the longer exposure of cells to Oxy133 (FIG. 3A). Oxy133 treatment also induced the expression of osteoblast-specific gene, osteocalcin, 2.8 fold after 4 days and reached a maximum of 4.2 fold after 14 days post-treatment (FIG. 3A). Oxy133 induced robust matrix mineralization in cultures of C3H cells as determined by von Kossa staining (FIG. 3B) and quantitative extracellular matrix 45 Ca assay after 21 days of treatment (FIG. 3C). These data demonstrate the efficacy and potency of Oxy133 as an osteoinductive oxysterol.

Figure 3D:
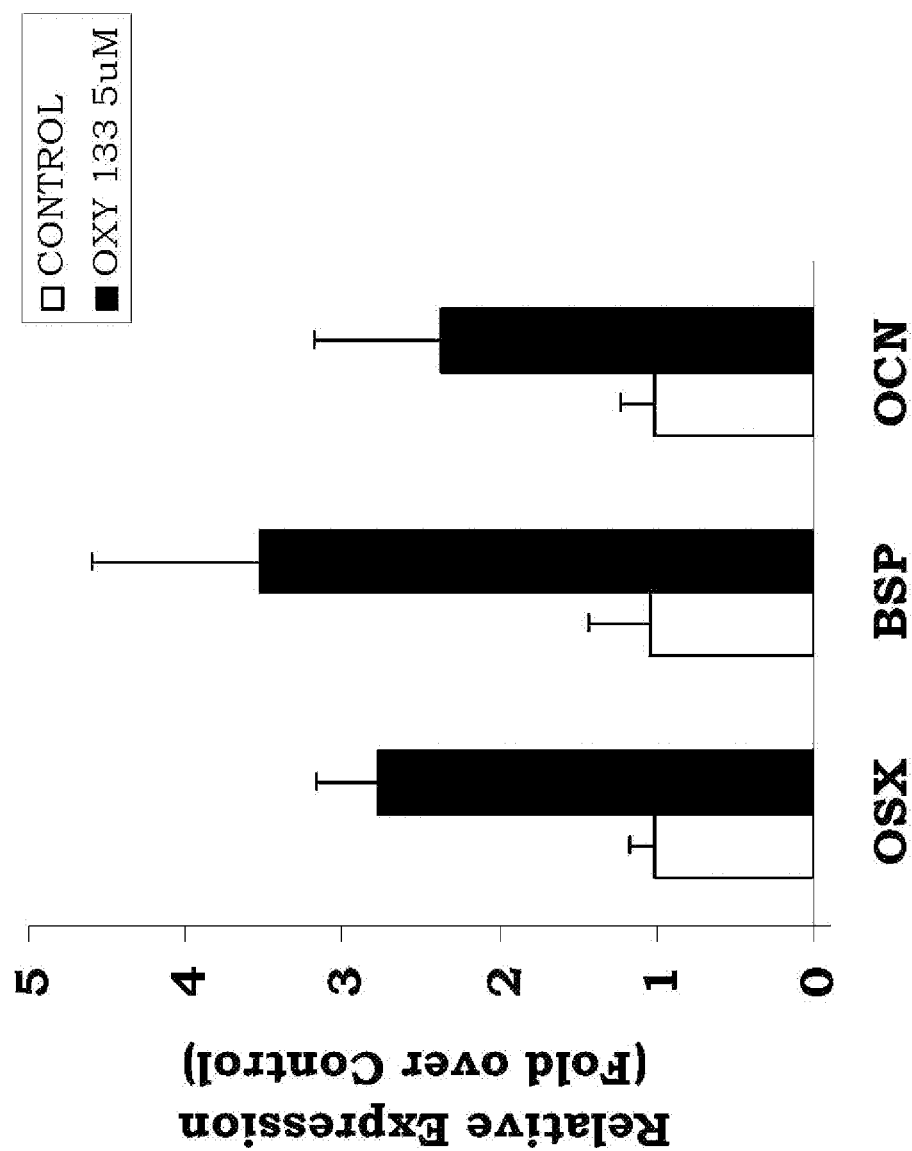
(FIG. 3D) Primary human MSC were treated in osteogenic medium with control vehicle or 5 µM Oxy133 for 4 weeks. Expression of osteogenic genes OSX, BSP, and OCN was measured by quantitative real-time PCR. Results from a representative experiment are reported as the mean of triplicate determination±SD ($p<0.05$ for all genes in control vs. Oxy133 treated cells).
Figure 3E:
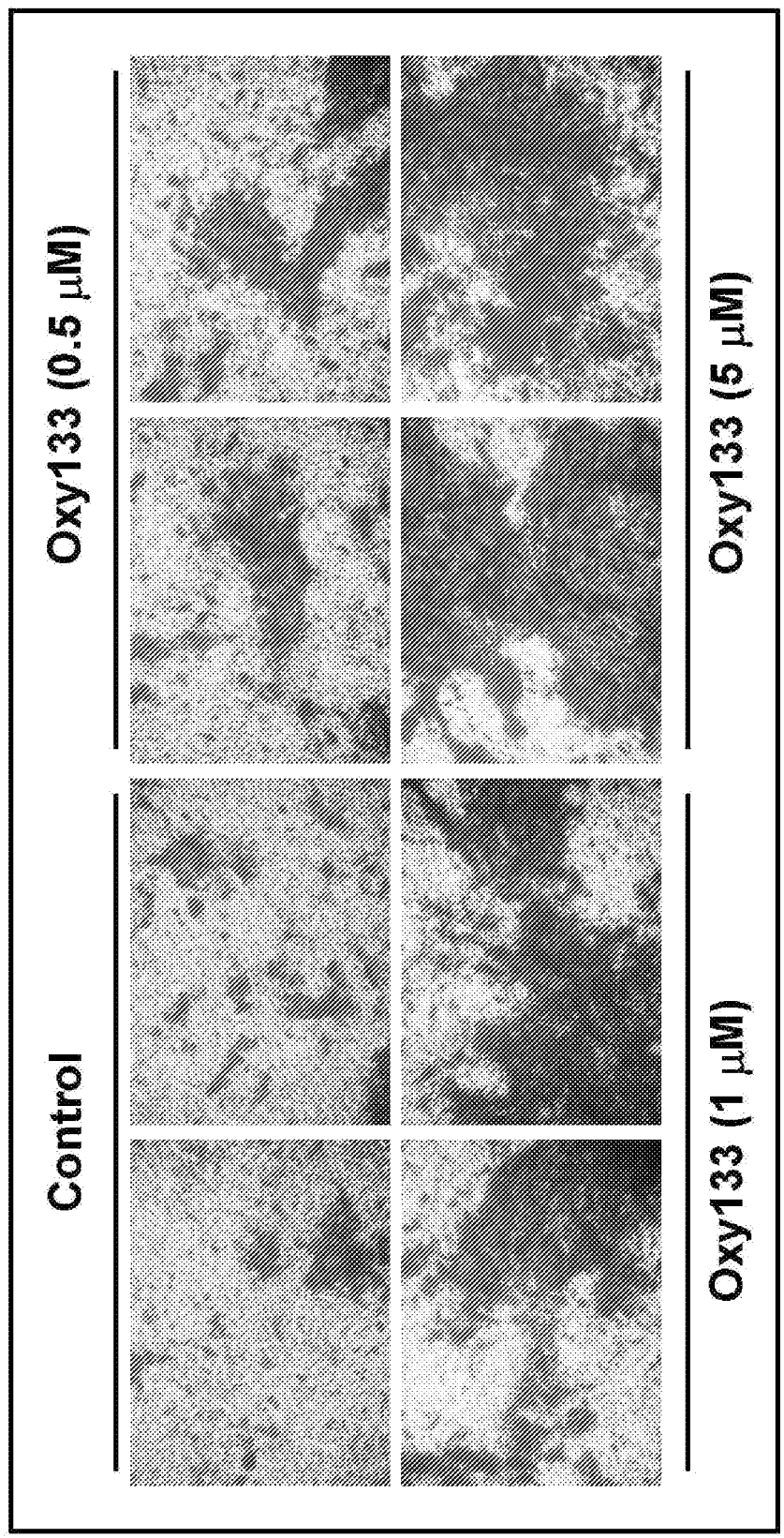
(FIG. 3E) Primary human MSC were treated in osteogenic medium with control vehicle or 0.5, 1, and 5 µM Oxy133 for 5 weeks. To examine extracellular mineralization von Kossa staining was performed and mineralized matrix appears as dark black staining under light microscopy (10×).

The osteogenic effects of Oxy133 were also examined in primary human mesenchymal stem cells (MSC) by assessing the expression of osteogenic genes 1 week, 2 weeks and 4 weeks post-treatment. ALP expression was high in untreated cells at all time points and there was no change with Oxy133 treatment (data not shown). After one week, a significant 2 fold increase in BSP expression was observed that was further increased to 4 fold after 2 and 4 weeks (FIG. 3D). Oxy133 also induced a significant induction of OSX (3 fold) and OCN (2 fold) after 4 weeks (FIG. 3D). Additionally, Oxy133 stimulated robust extracellular matrix mineralization in cultures of primary human MSC cells as demonstrated by von Kossa staining after 5 weeks of treatment (FIG. 3E).

Figure 4A:
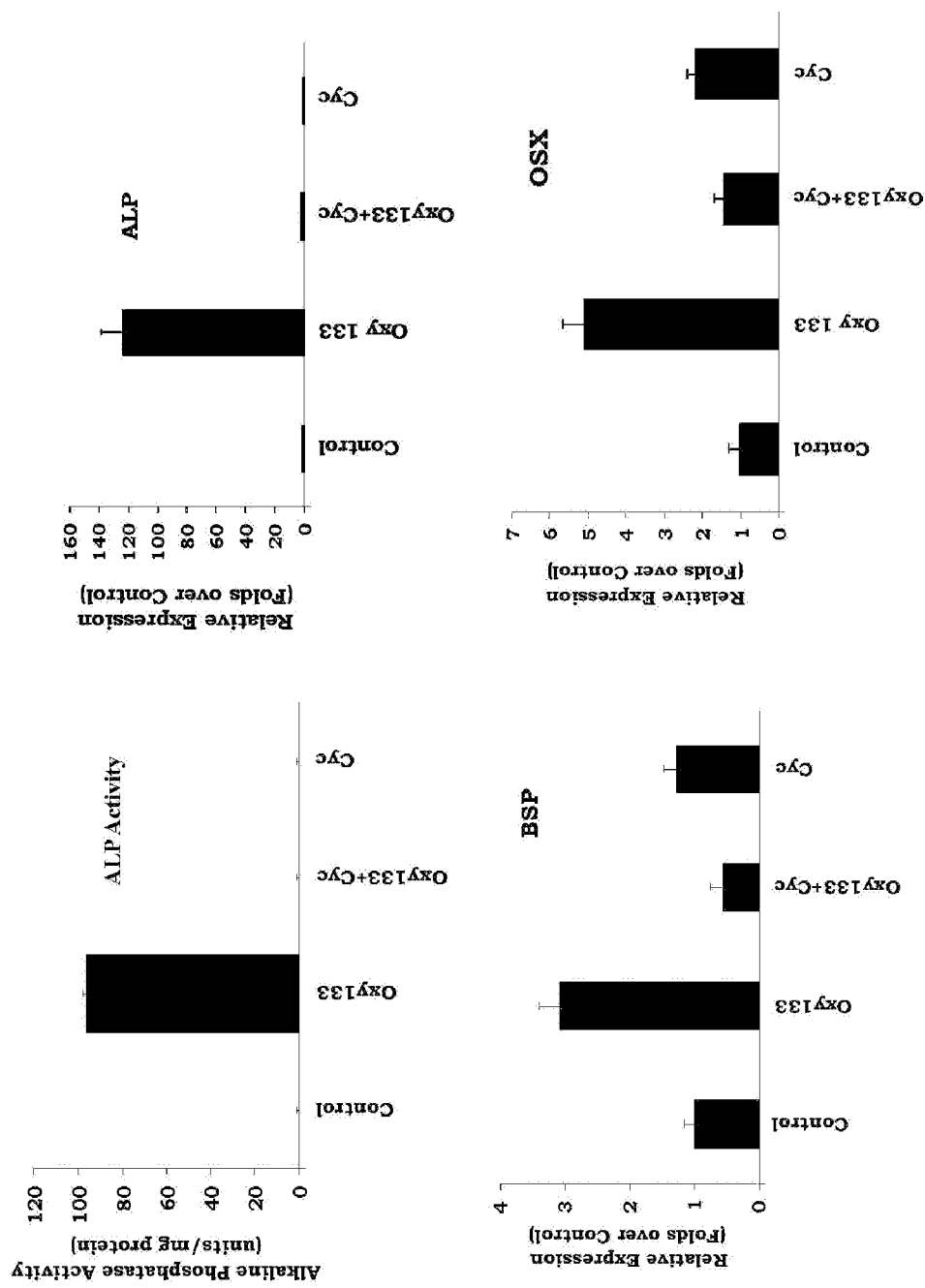
(FIG. 4A) C3H10T½ cells at confluence were treated in osteogenic medium with control vehicle or Oxy133 in the presence or absence of 4 µM cyclopamine (Cyc). After 4 days ALP activity, and after 7 days the expression of osteogenic genes ALP, BSP, and OSX was measured by quantitative real-time PCR ($p<0.001$ for control vs. Oxy133, and for Oxy133 vs. Oxy133+Cyc for ALP activity and for the expression of all genes shown).
Figure 4B:
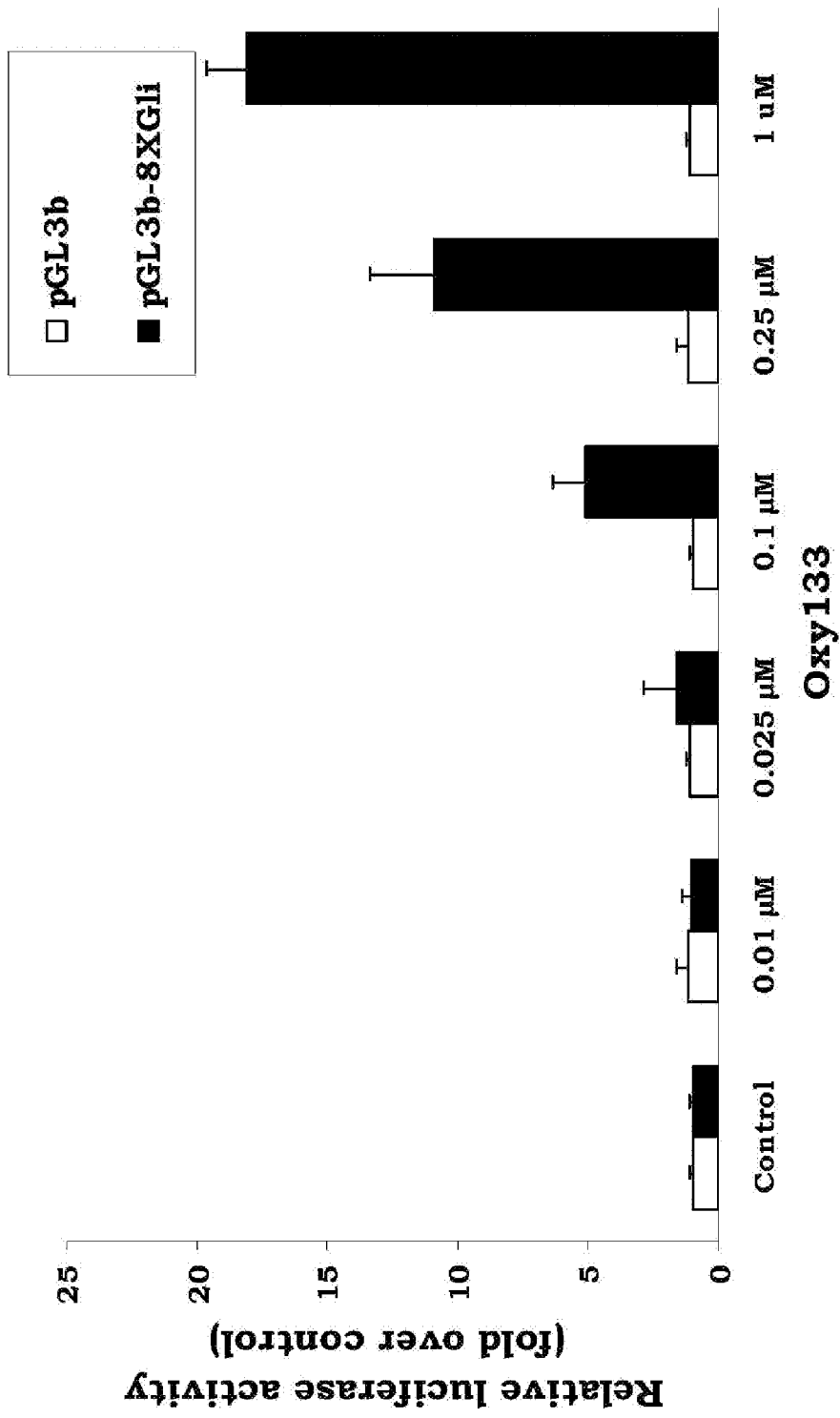
(FIG. 4B) C3H10T½ cells were transfected with control plasmid (pGL3b) or a plasmid containing 8×-Gli luciferase reporter and treated with control vehicle or Oxy133, and luciferase activity was determined after 48 hours. Results from a representative experiment are reported as the mean of triplicate determinations±SD. ($p<0.001$ for control vs. Oxy133 at 100 nM, 250 nM, and 1 µM Oxy133).

Oxy133 Induces Osteogenic Differentiation Through Activation of Hedgehog Pathway Signaling Prior research has demonstrated that 20S and its structural analogues Oxy34 and Oxy49 induce osteogenic differentiation via activation of Hh pathway signaling (15). However, the molecular mechanism for osteogenic oxysterol-mediated activation of Hh pathway signaling was not previously known. Given its greater osteogenic activity, Oxy133 is a useful tool for identifying the molecular mechanism by which Hh pathway activation and osteognesis are achieved by the semi-synthetic oxysterols. In order to determine whether and how Oxy133 induces osteogenic differentiation through the Hh pathway, the effect of the selective Hh pathway inhibitor, cyclopamine, on Oxy 133-induced ALP activity and expression of osteogenic differentiation markers ALP, BSP, and OSX was examined. Cyclopamine completely inhibited Oxy133-induced ALP activity and expression of osteogenic markers ALP, BSP, and OSX, in C3H cells (FIG. 4A), as well as in M2 cells (data not shown) suggesting that Oxy133 does act via the Hh signaling pathway. To further analyze the activation of Hh signaling by Oxy133, activation of a Gli-dependent luciferase reporter transfected into C3H cells was examined using previously reported methods (15, 17). Oxy133 induced a dose-dependent increase in activity of the Gli-dependent reporter, reaching a 5 fold induction at 100 nM and a 17 fold induction at 1 Oxy133 (FIG. 4B).

Figure 4C:
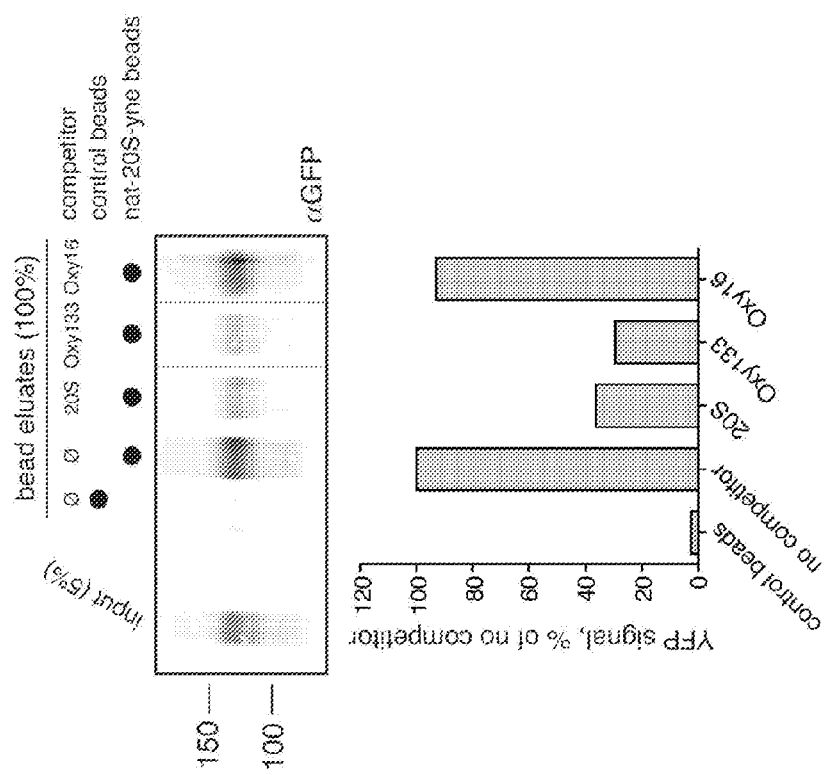
(FIG. 4C) The amount of YFP-Smo captured by 20S beads or control beads was compared in samples containing either no competitor or 50 µM of a free competitor sterol (20S, Oxy133 or Oxy16). The YFP-Smo captured by the beads was measured by Western blot (top) and plotted (bottom) relative to the amount captured in the binding reaction with no competitor.

Oxy133 Activates the Hedgehog Signaling Pathway by Binding to the Smoothened Receptor We previously reported that 20S selectively activates Hh signaling by binding to the Smo receptor (19). To determine whether Oxy133 activates Hh signaling by the same mechanism, we tested the ability of Oxy133 to compete for YFP-tagged Smo (YFP-Smo) binding with a 20S analogue coupled to magnetic beads. As we previously reported, this analogue, nat-20S-yne, contains an alkyne moiety on the iso-octyl chain, allowing for click chemistry-mediated coupling to magnetic beads (20S-beads) (19). Using these beads for sterol-binding assays, the amount of YFP-Smo remaining on the beads relative to a no-competitor sample is measured by Western blotting. Compounds that bind Smo at the same site as 20S compete with the 20S-beads and reduce the amount of protein in the eluate. We have tested many other sterols both in Smo binding assays and Hh signaling assays and in all cases binding to Smo correlated with a change in Hh pathway activity (19). Both Oxy133 and 20S, the positive control, reduced the amount of YFP-Smo captured on 20S-coupled beads (FIG. 4C). In an important control, a structurally related analogue, Oxy16, which cannot activate Hh signaling or osteogenesis (Parhami et al. unpublished observations) failed to prevent the interaction between YFP-Smo and 20S-beads (FIG. 4C). This reduction in the amount of YFP-Smo captured by 20S-beads in the presence of free Oxy133 suggests that Oxy133 binds to the same site on Smo as 20S. It is important to emphasize that our assay is semi-quantitative and cannot be used to derive Kd for the interaction, principally because we do not know the concentration of YFP-Smo in the extract and the amount of 20S productively immobilized on beads.

Oxy 133 Stimulates Bone Formation and Spinal Fusion In Vivo

Eight week old Lewis rats were divided into five treatment groups that differed only by the reagent contained within the collagen sponge at the surgery site: Group 1-control vehicle (DMSO) only (n=7), Group II-5 μg rhBMP-2 (n=8), Group III-20 mg Oxy133 (n=7), Group IV-2 mg Oxy133 (n=8), and Group V-0.2 mg Oxy133 (n=8). Bone formation and spinal fusion were assessed at various time points post-operatively through radiographic analysis, and at sacrifice using manual assessment, microcomputed tomography, and histology. Fusion rates at sacrifice are summarized in Table 1.

TABLE 1

Fusion Rates (%) Assessed with Plain Radiographs, Micro-CT, and Manual Palpation

|  | X-ray | Micro-CT | Manual Palpation |
| --- | --- | --- | --- |
| Control | 0 | 0 | 0 |
| BM P2 | 100 | 100 | 100 |

TABLE 1-continued

Fusion Rates (%) Assessed with Plain Radiographs, Micro-CT, and Manual Palpation

|  | X-ray | Micro-CT | Manual Palpation |
| --- | --- | --- | --- |
| Oxy133 20 mg | 100 | 100 | 86 |
| Oxy133 2 mg | 50 | 50 | 50 |
| Oxy133 0.2 mg | 0 | 0 | 0 |

Radiographic Analysis

Figure 5:
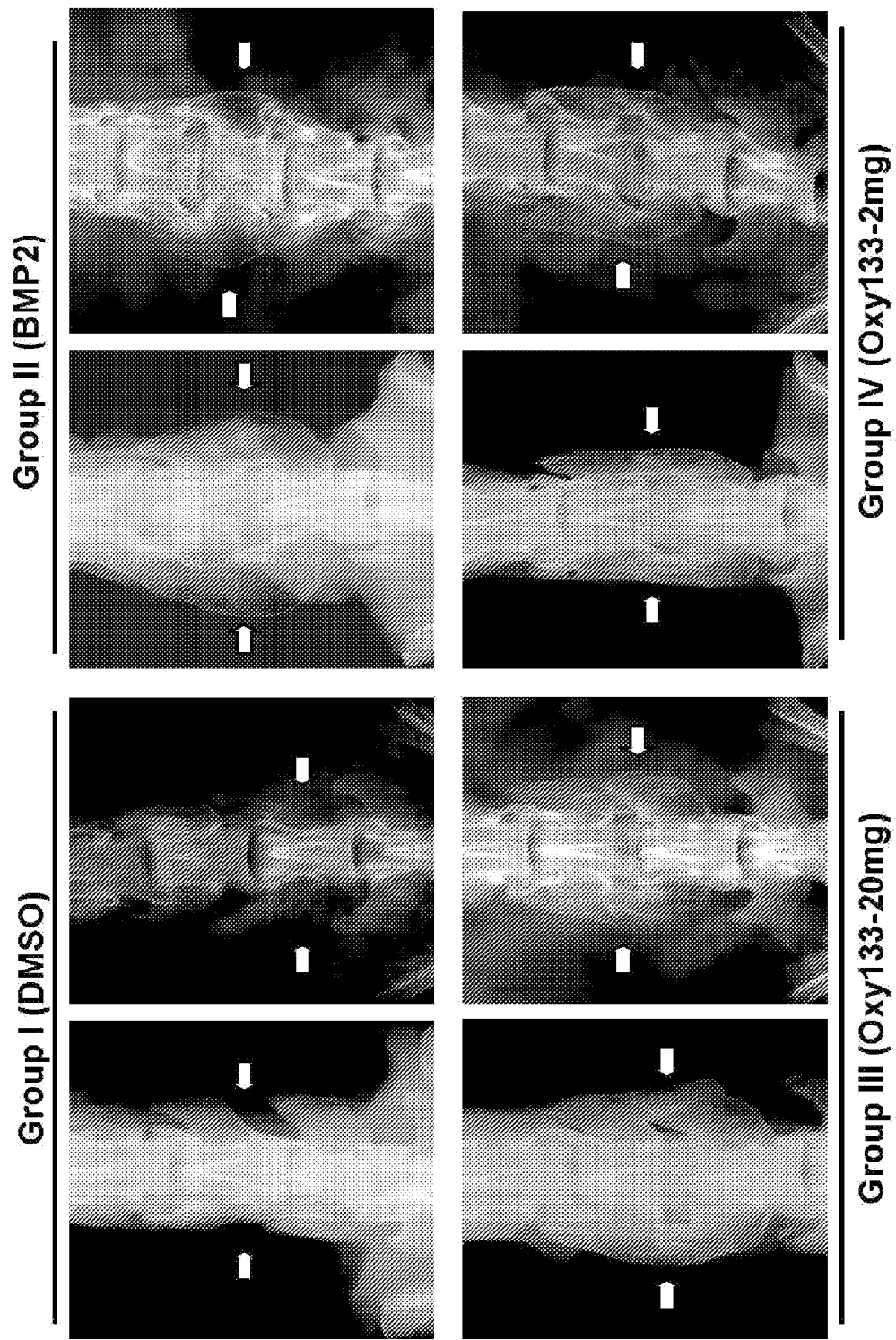
FIG. 5 shows plain radiographs of fusion masses formed by BMP2 and Oxy133. Faxitron images of two representative animals from the indicated groups at 8 weeks postoperatively are shown. Arrowheads signify lack of bone formation; arrows signify bone formation. Group I (Control); intertransverse process space with no bone formation. Group II (BMP2); bridging bone mass and bilateral fusion at L4-L5. Group III (Oxy133-20 mg); bridging bone mass and bilateral fusion at L4-L5. Group IV (Oxy133-2 mg); bridging bone mass and bilateral fusion at L4-L5 in animals that showed induction of fusion by Oxy133.

The first sets of radiographs were performed four weeks after the operation. At this time point, bilateral fusion was observed in 8/8 animals in the BMP2 group, 6/7 animals in the Oxy133-20 mg group, 3/8 animals in the Oxy133-2 mg group, and no fusion in the control and the Oxy133-0.2 mg groups. Unilateral fusion was observed in the remaining Oxy133-20 mg treated animal and in three animals treated with Oxy133-2 mg. This is in contrast to prior studies with Oxy34 and 49 in which no fusion was observed at the 4 week time point (15). By six weeks, all animals had fused bilaterally in the Oxy133-20 mg group. At eight weeks, fusion was again noted in all animals in the BMP2 and Oxy133-20 mg groups and in 4/8 of the Oxy133-2 mg group (FIG. 5). No fusion mass was observed in the DMSO or Oxy133-0.2 mg (data not shown) groups in the final eight week radiographs (FIG. 5).

Manual Assessment and Gross Evaluation of Bone Formation

After sacrifice, the spines were explanted from each animal and subjected to manual assessment as we have previously described (15, 25-27). Gross evaluation and manual assessment results were similar to radiographic findings at 8 weeks. No unilateral or bilateral fusion was observed in the DMSO or Oxy133-0.2 mg groups. Some bone formation was noted in two animals in the Oxy133-0.2 mg group. Bilateral fusion was observed in all animals in the BMP2 group and 6/7 animals in the Oxy133-20 mg group. The remaining animal in the Oxy 133-20 mg group had motion unilaterally despite significant bilateral fusion mass. Half (4/8) of the animals in the Oxy133-2 mg group had bilateral fusion confirmed on manual palpation while two additional animals had unilateral fusion and two animals had no evidence of fusion.

Micro-Computed Tomography and Histological Assessment

Figure 6:
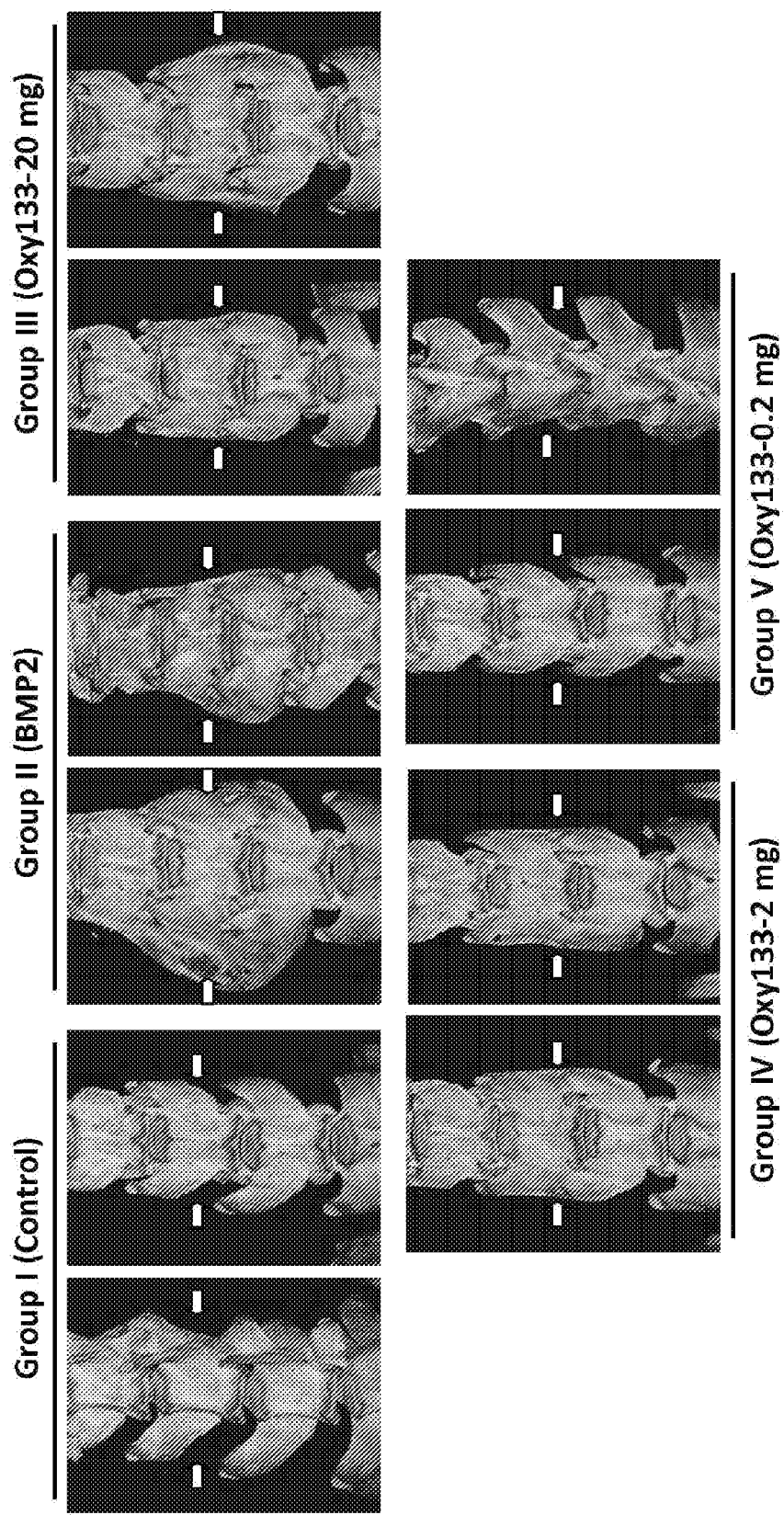
FIG. 6 shows microCT of fusion masses formed by BMP2 and Oxy133. Micro CTs of two representative animals from the indicated groups are shown. Arrowheads signify lack of bone formation; arrows signify bone formation. Group I (Control); intertranverse process space with no bone formation. Group II (BMP2); bone mass bridging the intertransverse process space and bilateral fusion at L4-L5. Group III (Oxy133-20 mg); bone mass bridging the intertransverse process space and bilateral fusion at L4-L5. Group IV (Oxy133-2 mg); bone mass bridging the intertransverse process space and bilateral fusion at L4-L5 in animals that showed induction of fusion by Oxy133. Group V (Oxy133-0.2 mg); arrow on the far right indicates a small amount of bone formation from the L5 transverse process.

Assessment of bridging trabecular bone with micro-CT analysis confirmed results observed with radiographs, gross observation, and manual palpation (FIG. 6). Although some bone formation was seen in two animals in the Oxy133-0.2 mg group, no bilateral fusions were observed in this group or the DMSO group. Bilateral bridging trabecular bone was seen in all animals in the BMP2 group and the Oxy133-20 mg group. Bilateral fusion was also observed in 4/8 animals in the Oxy133-2 mg group with unilateral fusion in two additional animals. The results of the microstructural analysis from the micro-CT images are shown in Table 2. The total volume of the BMP2 fusion masses was significantly greater than both the Oxy133-2 mg and 20-mg samples. However, the mean BV/TV ratio of the Oxy133-2 mg and 20-mg fusion masses was significantly greater than the BMP2 group, indicating denser bone within the masses. Trabecular thickness did not significantly differ between BMP2 and either Oxy133-2 mg or Oxy133-20 mg. Trabecular separation was significantly larger in the BMP2 fusion masses compared to Oxy133-2 mg and Oxy133-20 mg, also indicating less density of bone in the BMP2 fusion masses.

TABLE 2

Quantitative Assessment of Bone Microstructure from Micro-CT Imaging

|  | Fusion Mass Total Tissue Volume (mm³) | Fusion Mass Bone Volume (mm³) | Fusion Mass Bone Volume to Tissue Volume (%) | | Fusion Mass Trabecular Separation (μm) |
| --- | --- | --- | --- | --- | --- |
| BMP2 5 μg | 106.909* | 20.126 | 19.633* | 131.131 | 446.126* |
| Oxy133 2 mg | 78.586 | 21.217 | 27.104 | 134.008 | 321.693 |
| Oxy133 20 mg | 79.934 | 19.592 | 24.565 | 124.737 | 310.912 |

* indicates statistically significant difference (p < 0.01) in total tissue volume, bone volume to tissue volume ratio, and trabecular separation between BMP2 and Oxy133 20 mg and 2 mg. No differences were observed in bone volume or trabecular thickness.

Figure 7A:
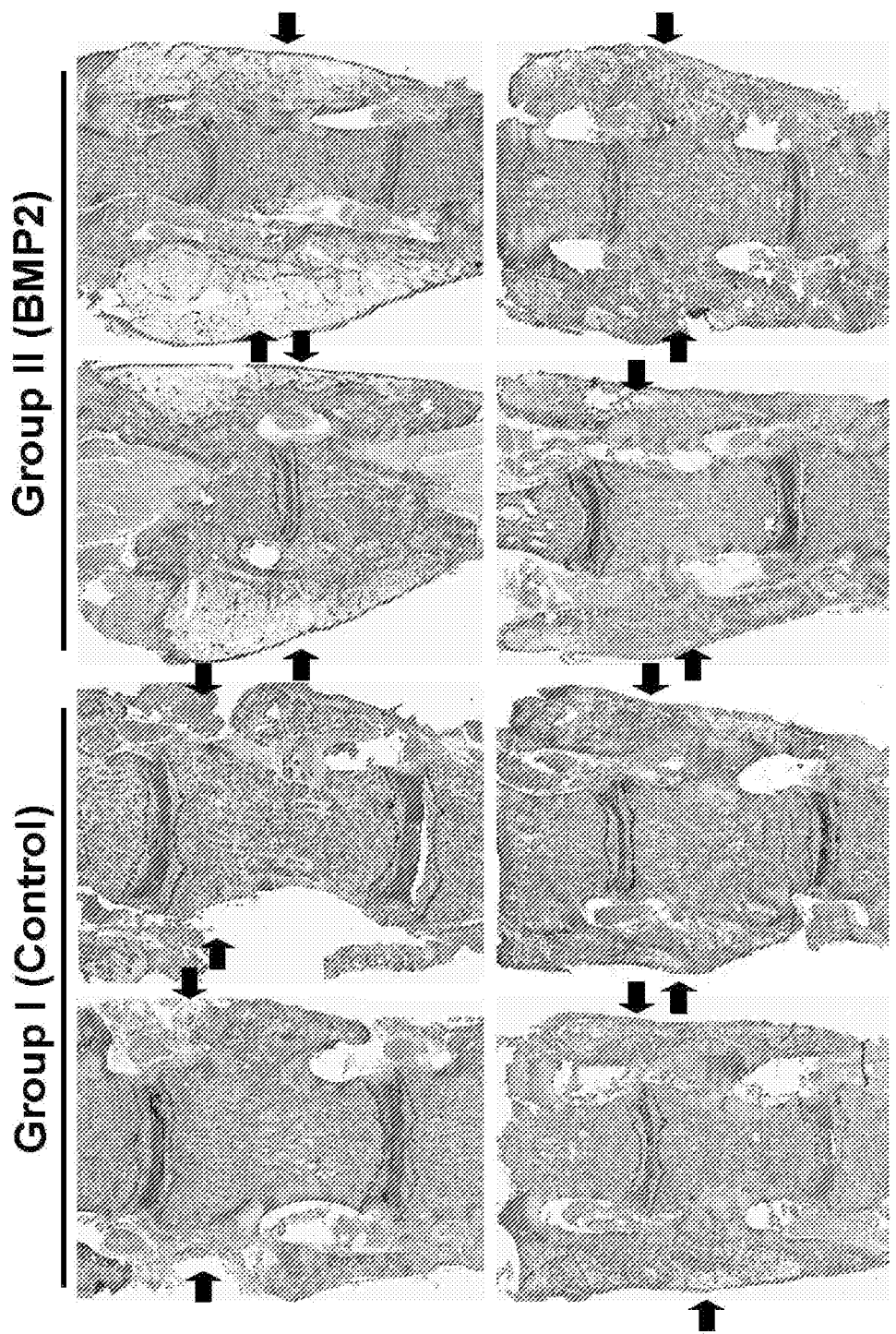
(FIG. 7A) Coronal histological sections of two separate representative animals from each group are shown (10×). Group I (Control) has no significant bone formation at the intertransverse process space (arrowheads). Group II (BMP2) demonstrates bridging bone at L4-L5 (arrows) with clear evidence of trabecular and cortical bone forming the fusion mass. Group III (Oxy133-20 mg) and Group IV (Oxy133-2 mg) specimens demonstrate significant bone formation at the intertransverse process space (arrows) with trabecular and cortical bone formation comparable to that induced by BMP2.
Figure 7B:
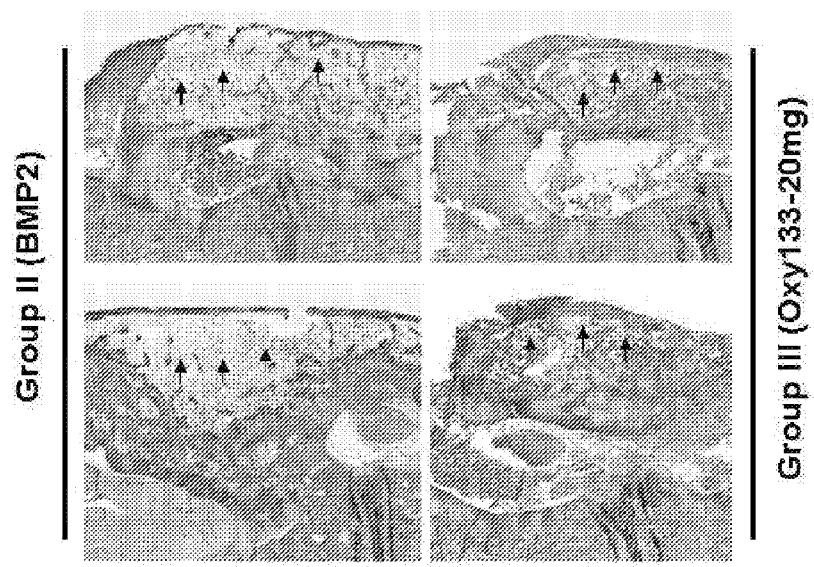
(FIG. 7B) Coronal histological sections from two animals each in Groups II (BMP2) and Group III (Oxy133-20 mg) demonstrate significant adipocyte formation in the fusion mass of BMP2 treated animals and substantially fewer adipocytes in the fusion mass from oxysterol treated animals (arrows, magnification 20×).

Histologic analysis was then performed in two representative animals in the DMSO group, BMP2 group, Oxy133-20 mg group, and Oxy133-2 mg group. Histological assessment demonstrated the formation of trabecular bone within the fusion mass and continuous cortical bone connecting the transverse processes of the fully fused lumbar vertebrae in rats treated with BMP2, or with the 2 or 20 mg dose of Oxy133 (FIG. 7A). Bone formation was not present in specimens from control rats. The size of the fusion mass was increased in rats treated with BMP2 compared to 20 mg or 2 mg of Oxy133. However, visual inspection of the histological specimens indicated that BMP2 also induced robust formation of adipocytes within the fusion mass, which was significantly less in groups treated with Oxy 133 (FIG. 7B). In addition, visual inspection suggested that trabecular bone formation was more robust in the Oxy133-20 mg group compared with BMP2 group.

Example IV

Inhibition of Adipogenesis

Using conventional procedures, C3H10T½ osteo-adipo-progenitor cells were treated with the PPARgamma activator, Troglitazone ("Tro"), which has been reported to induce adipocyte formation. After two weeks, adipogenesis in the Tro treated wells was visualized by Oil Red O staining and the adipocytes quantified by light microscopy. It was clear that Oxy133 at a dose that induces both osteogenic differentiation and Hh signaling completely inhibited adipocyte formation. The following are the data (as average adipocytes per field of view≠SD):

view≠SD):

Control: 2.5≠2

Tro: 28≠4

Tro+Oxy133 (5 uM): 0.5≠1

Oxy133 (5 uM): 0.8≠1

The p value for control vs. Tro vs. Tro+Oxy133 reached significance at <0.01

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional application 61/643,746, filed May 7, 2012, are hereby incorporated by reference in their entirety, particularly with regard to the disclosure for which they are cited in the application. Also incorporated by reference in their entirely are other applications concerning oxysterols from the present inventor's laboratory, including Patent Cooperation Treaty (PCT) international applications published as WO/2008/115469, WO/2008/082520, WO/2007/098281, WO/2007/028101, WO/2006/110490, WO/2005/020928, and WO/2004/019884.

REFERENCES

1. Johnson E E, Urist M R 2000 Human bone morphogenetic protein allografting for reconstruction of femoral non-union. Clin Orthop Relat Res 371:61-74.
2. Mundy G R 2002 Directions of drug discovery in osteoporosis. Annu Rev Med 53:337-54.
3. Rodan G A, Martin T J 2000 Therapeutic Approaches to Bone Diseases. Science 289:1508-14.
4. Yoon S T, Boden S D 2002 Osteoinductive molecules in orthopaedics: basic science and preclinical studies. Clin Orthop Relat Res 395:33-43.
5. Arrington E D, Smith W J, Chambers H G, Bucknell A L, Davino N A 1996 Complications of iliac crest bone graft harvesting. Clin Orthop Relat Res 329:300-9.
6. Vaccaro A R, Chiba K, Heller J G, Patel T C, Thalgott J S, Truumees E, Fischgrund J S, Craig M R, Berta S C, Wang J C 2002 Bone grafting alternatives in spinal surgery. Spine J 2:206-15.
7. Rihn J A, Kirkpatrick K, Albert T J 2010 Graft options in posterolateral and posterior interbody lumbar fusion. Spine 35:1629-39.
8. Mitka M 2011 Questions about spine fusion product prompt a new process for reviewing data. JAMA 306:1311-2.
9. Lewandrowski K-U, Nanson C, Calderon R 2007 Vertebral osteolysis after posterior interbody lumbar fusion with recombinant human bone morphogenetic protein 2: a report of five cases. Spine J 7:609-14.
10. Wong D A, Kumar A, Jatana S, Ghiselli G, Wong K 2008 Neurologic impairment from ectopic bone in the lumbar canal: a potential complication of off-label PLIF/TLIF use of bone morphogenetic protein-2 (BMP-2). Spine J 8:1011-8.
11. Smucker J D, Rhee J M, Singh K, Yoon S T, Heller J G 2006 Increased swelling complications associated with off-label usage of rhBMP-2 in the anterior cervical spine. Spine. 31:2813-9.
12. Carragee E J, Hurwitz E L, Weiner B K 2011 A critical review of recombinant human bone morphogenetic protein-2 trials in spinal surgery: emerging safety concerns and lessons learned. Spine J 11:471-91.
13. Kha H T, Basseri B, Shouhed D, Richardson J, Tetradis S, Hahn T J, Parhami F 2004 Oxysterols regulate differentiation of mesenchymal stem cells: pro-bone and anti-fat. J Bone Miner Res 19:830-40.
14. Kim W-K, Meliton V, Amantea C M, Hahn T J, Parhami F 2007 20(S)-hydroxycholesterol inhibits PPARgamma expression and adipogenic differentiation of bone marrow stromal cells through a Hedgehog-dependent mechanism. J Bone Miner Res 22:1711-9.
15. Johnson J S, Meliton V, Kim W K, Lee K-B, Wang J C, Nguyen K, Yoo D, Jung M E, Atti E, Tetradis S, Pereira R C, Magyar C, Nargizyan T, Hahn T J, Farouz F, Thies S, Parhami F 2011 Novel oxysterols have pro-osteogenic and anti-adipogenic effects in vitro and induce spinal fusion in vivo. J Cell Biochem 112:1673-84.
16. Parhami F, Morrow A D, Balucan J, Leitinger N, Watson A D, Tintut Y, Berliner J A, Demer L L 1997 Lipid oxidation products have opposite effects on calcifying vascular cell and bone cell differentiation. A possible explanation for the paradox of arterial calcification in osteoporotic patients. Arterioscler Thromb Vasc Biol 17:680-7.
17. Dwyer J R, Sever N, Carlson M, Nelson S F, Beachy P A, Parhami F 2007 Oxysterols are novel activators of the Hedgehog signaling pathway in pluripotent mesenchymal cells. J Biol Chem 282:8959-68.
18. Kim W-K, Meliton V, Bourquard N, Hahn T J, Parhami F 2010 Hedgehog signaling and osteogenic differentiation in multipotent bone marrow stromal cells are inhibited by oxidative stress. J Cell Biochem 111:1199-209.
19. Nachtergaele S, Mydock L K, Krishnan K, Rammohan J, Schlesinger P H, Covey D F, Rohatgi R 2012 Oxysterols are allosteric activators of the oncoprotein Smoothened. Nat Chem Biol 8:211-20.
20. Rohatgi R, Milenkovic L, Corcoran R B, Scott M P 2009 Hedgehog signal transduction by Smoothened: pharmacologic evidence for a 2-step activation process. Proc Natl Acad Sci USA 106:3196-201.
21. Alanay A, Chen C, Lee S, Murray S S, Brochmann E J, Miyazaki M, Napoli A, Wang J C 2008 The adjunctive effect of a binding peptide on bone morphogenetic protein enhanced bone healing in a rodent model of spinal fusion. Spine 33:1709-13.
22. Miyazaki M, Sugiyama O, Tow B, Zou J, Morishita Y, Wei F, Napoli A, Sintuu C, Lieberman J R, Wang J C 2008 The effects of lentiviral gene therapy with bone morphogenetic protein-2-producing bone marrow cells on spinal fusion in rats. J Spinal Disord Tech 21:372-9.
23. Pereira R C, Stadmeyer L E, Smith D L, Rydziel S, Canalis E 2007 CCAAT/Enhancer-binding protein homologous protein (CHOP) decreases bone formation and causes osteopenia. Bone 40:619-26.
24. Magyar C E, Aghaloo T L, Atti E, Tetradis S 2008 Ostene, a new alkylene oxide copolymer bone hemostatic material, does not inhibit bone healing. Neurosurgery 63:373-378; discussion 378.
25. Sintuu C, Simon R J, Miyazaki M, Morishita Y, Hymanson H J, Taghavi C, Brochmann E J, Murray S S, Wang J C 2011 Full-length spp24, but not its 18.5-kDa proteolytic fragment, inhibits bone-healing in a rodent model of spine fusion. J Bone Joint Surg Am 93:1022-32.
26. Miyazaki M, Morishita Y, He W, Hu M, Sintuu C, Hymanson H J, Falakassa J, Tsumura H, Wang J C 2009 A porcine collagen-derived matrix as a carrier for recombinant human bone morphogenetic protein-2 enhances spinal fusion in rats. Spine J 9:22-30.
27. Zhu W, Rawlins B A, Boachie-Adjei O, Myers E R, Arimizu J, Choi E, Lieberman J R, Crystal R G, Hidaka C 2004 Combined bone morphogenetic protein-2 and -7 gene transfer enhances osteoblastic differentiation and spine fusion in a rodent model. J Bone Miner Res 19:2021-32.

We claim:
1. A compound having the structure:

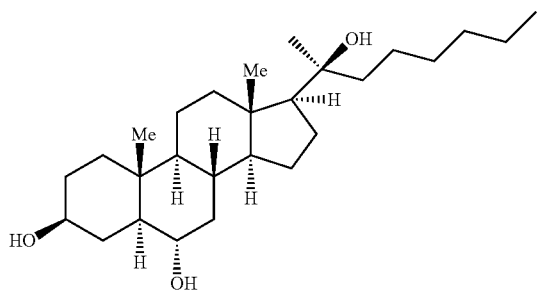

or a pharmaceutically acceptable salt or solvate thereof.
2. A composition, comprising a pharmaceutically acceptable carrier and a compound having the structure:

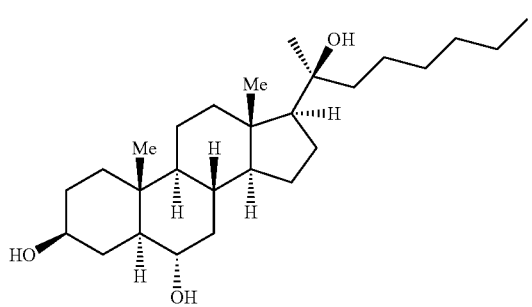

or a pharmaceutically acceptable salt or solvate thereof.
3. The composition of claim 2, further comprising at least one additional agent, selected from the group consisting of parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, BMP 2, BMP 4, BMP 7, BMP 14, and combinations thereof.
4. A method for treating a subject having a bone disorder, osteoporosis, or a bone fracture, comprising administering to the subject an effective amount of the composition of claim 2.
5. The method of claim 4, comprising administering to the subject the composition at a therapeutically effective dose in an effective dosage form at a selected interval to increase bone mass.
6. The method of claim 4, comprising administering to the subject the composition at a therapeutically effective dose in an effective dosage form at a selected interval to ameliorate the symptoms of osteoporosis.
7. A method for treating a subject in need of an increase in osteomorphogenesis and/or osteoproliferation, comprising administering to the subject an effective amount of the composition of claim 2.
8. A method for treating a subject to induce bone formation, comprising administering the composition of claim 2 in an effective dosage form at a selected interval to increase bone mass.
9. The method of claim 4, wherein the composition is administered locally to a cell, tissue or organ in the subject.
10. An implant for use in a human or animal body comprising a substrate having a surface, wherein the surface or the insides of the implant comprises the composition of claim 2 in an amount sufficient to induce bone formation in the surrounding bone tissue.

11. The implant of claim 10, wherein the substrate is formed into the shape of a pin, screw, plate, or prosthetic joint.

\* \* \* \* \*